(12) United States Patent
Ryffel et al.

(10) Patent No.: US 8,569,017 B2
(45) Date of Patent: Oct. 29, 2013

(54) METHOD FOR THE PREVENTING AND/OR TREATING IL-1 BETA LUNG PATHOLOGY IN MAMMALS BY ADMINISTERING A URIC ACID REDUCING COMPOUND

(75) Inventors: Bernhard Ryffel, Saint Denis en Val (FR); Isabelle Couillin, Avaray (FR)

(73) Assignee: Centre National de la Recheche Scientifique (CNRS), Paris (FR)

( * ) Notice: Subject to any disclaimer, the term of this patent is extended or adjusted under 35 U.S.C. 154(b) by 0 days.

(21) Appl. No.: 13/119,363

(22) PCT Filed: Sep. 18, 2009

(86) PCT No.: PCT/EP2009/062159
§ 371 (c)(1),
(2), (4) Date: Jun. 6, 2011

(87) PCT Pub. No.: WO2010/031859
PCT Pub. Date: Mar. 25, 2010

(65) Prior Publication Data
US 2011/0243911 A1    Oct. 6, 2011

(30) Foreign Application Priority Data
Sep. 18, 2008  (EP) .................................. 083055657

(51) Int. Cl.
*C12N 15/09*    (2006.01)
(52) U.S. Cl.
USPC ........................................... 435/69.2; 436/99
(58) Field of Classification Search
USPC ........................................... 435/69.2; 436/99
See application file for complete search history.

(56) References Cited

U.S. PATENT DOCUMENTS

2008/0286316 A1* 11/2008 Kay ............................ 424/278.1

FOREIGN PATENT DOCUMENTS

| WO | WO 2005/030138 | * | 4/2005 |
| WO | WO 2005/030138 A3 | | 4/2005 |
| WO | WO 2008/151235 A2 | | 12/2008 |

OTHER PUBLICATIONS

Gasse, P. IL-1R1/MyD Signaling and the Infllammasome are Essential in Pulmonary Inflammation and Fibrosis in Mice J of Clinical Investigation 117(12)3786-3799.*
Bianchi M.E., "DAMPs, PAMPs and alarmins: all we need to know about danger," J. Leukoeyte Biology, Jan. 2007, pp. 1-5, vol. 81.
Cammalleri et al., "Rasburicase represents a new tool for hyperuricemia in tumor lysis syndrome and in gout," Int J Med Sci, 2007, pp. 83-93, vol. 4.
Chen et al., "Identification of a key pathway required for the sterile inflammatory response triggered by dying cells," Nat Med., Jul. 2007, pp. 851-856, vol. 13, No. 7.

Chen et al., "MyD88-dependent IL-1 receptor signaling is essential for gouty inflammation stimulated by monosodium urate crystals," J. Clin. Invest., Aug. 2006, pp. 2262-2271, vol. 116, No. 8.
European Search Report, App. No. EP 08 30 5565, 2 pages, dated Feb. 13, 2009.
Feldmeyer et al., "The Inflammasome Mediates UVB-Induced Activation and Secretion of Interleukin-1β by Keratinocytes," Curr Biol, Jul. 2007, pp. 1140-1145, vol. 17.
Gallucci et al., "Natural adjuvants: Endogenous activators of dendritic cells," Nat Med, Nov. 1999, pp. 1249-1255, vol. 5, No. 11.
Gasse et al., "IL-1R1/MyD88 signaling and the inflammasome are essential in pulmonary inflammation and fibrosis in mice," J Clin Invest, Dec. 2007, pp. 3786-3799, vol. 117, No. 12.
Gross et al., "Idiopathic Pulmonary Fibrosis," N. Engl. J. Med, Aug. 2001, pp. 517-525, vol. 345, No. 7.
Hamilton et al., "Bleomycin induces apoptosis in human alveolar macrophages," Am J Physiol, 1995, pp. L318-L325, vol. 269.
International Search Report, Int'l App. No. PCT/EP2009/062159, 3 pages, dated Jan. 14, 2010.
Lappalainen et al., "Interleukin-1β Causes Pulmonary Inflammation, Emphysema, and Airway Remodeling in the Adult Murine Lung," Am J Respiratory Cell and Molecular Biology, 2005, pp. 311-318, vol. 32, No. 4.
Liu-Bryan et al., "Innate Immunity Conferred by Toll-like Receptors 2 and 4 and Myeloid Differentiation Factor 88 Expression Is Pivotal to Monosodiurri Urate Monohydrate Crystal-Induced Inflammation," Arthritis & Rheum, Sep. 2005, 2936-2946, vol. 52, No. 9.
Mariathasan et al., "Cryopyrin activates the inflammasome in response to toxins and ATP," Nature, Mar. 2006, pp. 228-232, vol. 440.
Mariathasan et al., "Inflammasome adaptors and sensors: intracellular regulators of infection and inflammation," Nat Rev Immunol, Jan. 2007, pp. 31-40, vol. 7.
Martinon et al., "Gout-associated uric acid crystals activate the NALP3 inflammasome," Nature, Mar. 2006, pp. 237-241, vol. 440.
Matzinger P., "The Danger Model: A Renewed Sense of Self," Science, Apr. 2002, pp. 301-305, vol. 296.
Moolenburgh et al., "Rasburicase treatment in severe tophaceous gout: a novel therapeutic option," Clin. Rheumatol, 2006, pp. 749-752, vol. 25.

(Continued)

*Primary Examiner* — Ralph Gitomer
(74) *Attorney, Agent, or Firm* — Foley & Lardner LLP

(57) ABSTRACT

The present invention is directed to the use of a compound capable of reducing the uric acid level in a mammal for the prevention and/or the treatment of IL-Iβ driven lung pathology, particularly to treat lung inflammation such as chronic fibrosis, COPD and interstitial fibrosis and other IL-1β driven lung pathologies including those of autoimmune origin. Preferred compounds capable of reducing the uric acid level are selected from the group consisting of xanthine oxidase inhibitors, such as allopurinol, recombinant enzyme uricase and uricosuric compound capable of enhancing uric acid excretion, such as probenecid. The invention further relates to a method for identifying in vitro whether a patient presents an IL-1β driven lung pathology or is at risk to develop an IL-1β driven lung pathology, or for the screening of a compound for treating an IL-1β driven lung pathology.

8 Claims, 27 Drawing Sheets

(56) References Cited

OTHER PUBLICATIONS

Figure 1B:
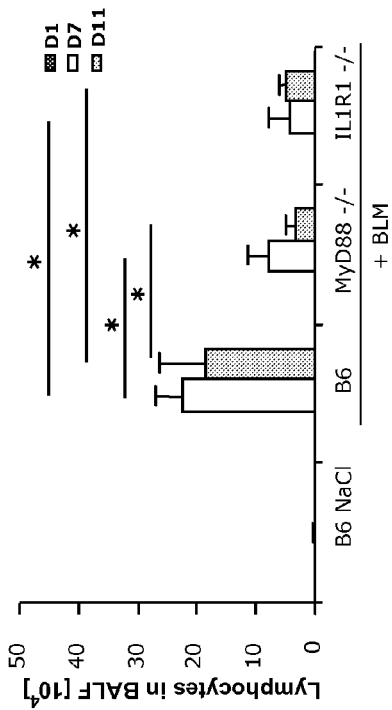
Figure 1D:
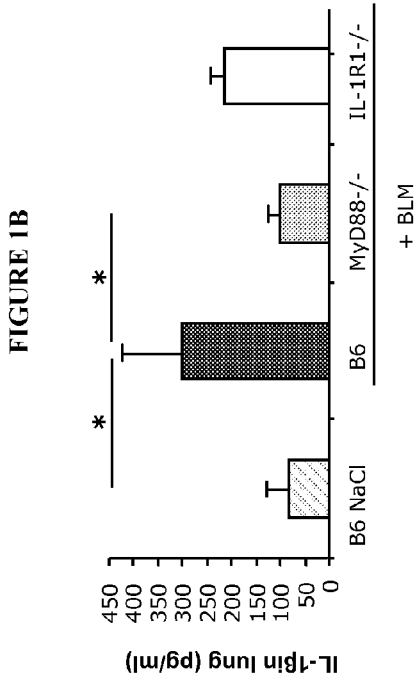
Figure 1A:
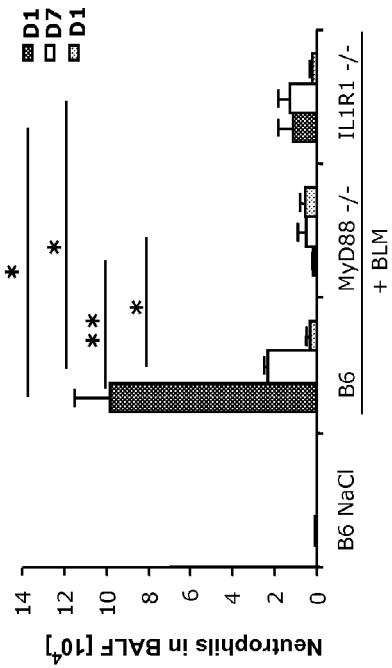
Figure 1C:
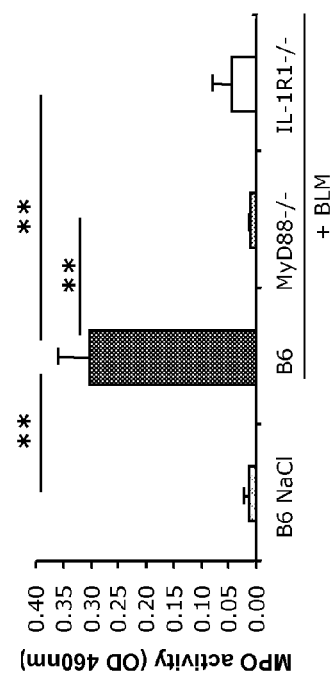
Figure 1E:
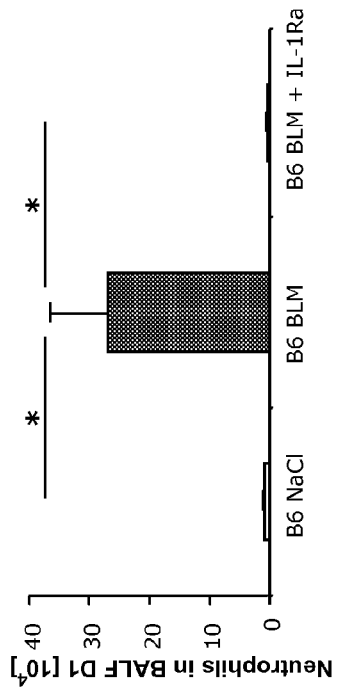
Figure 1F:
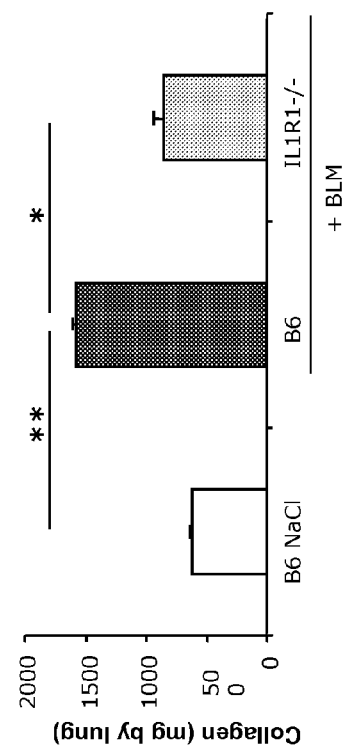
Figure 2A:
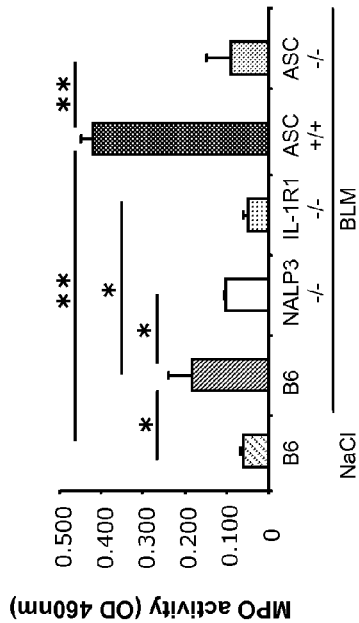
Figure 2B:
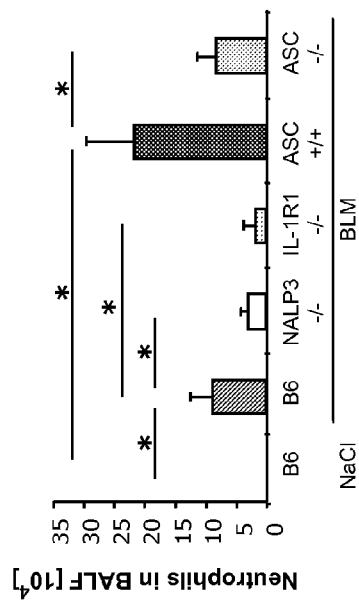
Figure 2D:
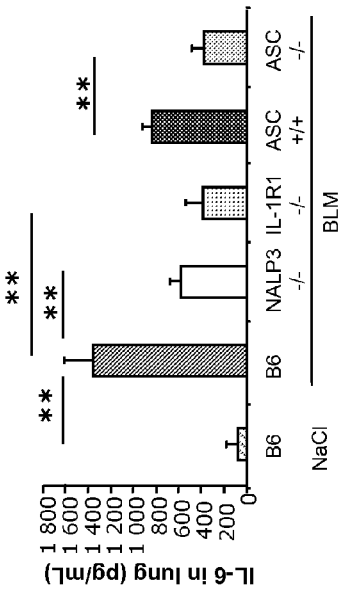
Figure 2F:
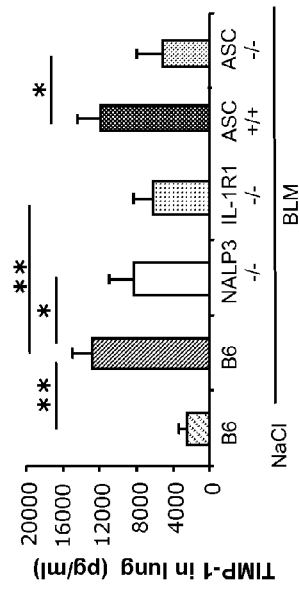
Figure 2C:
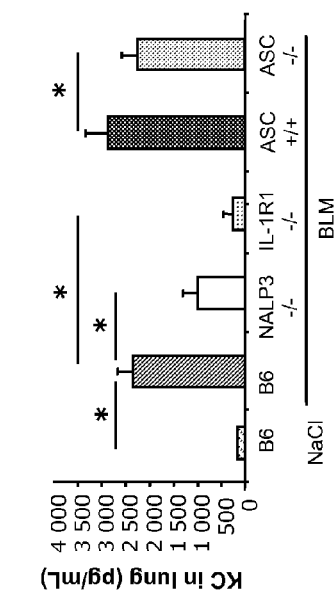
Figure 2E:
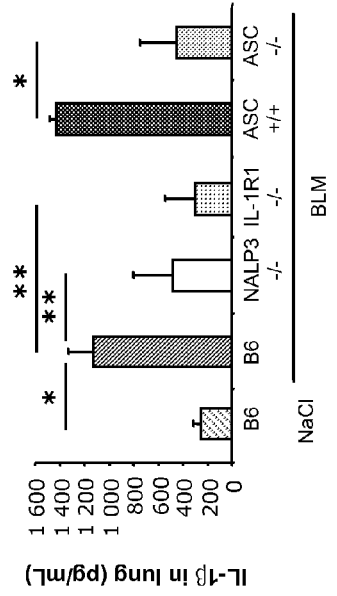

Parks et al., "Multiple organ dysfunction syndrome: Role of xanthine oxidase and nitric oxide," Pathophysiology, 1998, pp. 49-66, vol. 5, No. 1.

Rock et al., "Natural endogenous adjuvants," Springer Semin Immunopathol, 2005, pp. 231-246, vol. 26.

Sauter et al., "Consequences of Cell Death: Exposure to Necrotic Tumor Cells, but Not Primary Tissue Cells or Apoptotic Cells, Induces the Maturation of Immunostimulatory Dendritic Cells," J Exp Med, Feb. 2000, pp. 423-433, vol. 191, No. 3.

Scaffidi et al., "Release of chromatin protein HMGB1 by necrotic cells triggers inflammation," Nature, 2002, pp. 191-195, vol. 418.

Shenkar et al., "Mechanisms of Lung Neutrophil Activation After Hemorrhage or Endotoxemia: Roles of Reactive Oxygen Intermediates, NF-κB, and Cyclic AMP Response Element Binding Protein," J Immunology, 1999, pp. 954-962, vol. 163, No. 2.

Shi et al., "Molecular identification of a danger signal that alerts the immune system to dying cells," Nature, Oct. 2003, pp. 516-521, vol. 425.

Sutterwala et al., "Critical Role for NALP3/CIAS1/Cryopyrin in Innate and Adaptive Immunity through Its Regulation of Caspase-1," Immunity, Mar. 2006, pp. 317-327, vol. 24.

Terkeltaub R. A., "Clinical Practice. Gout," N. Engl. J. Med., Oct. 2003, pp. 1647-1655, vol. 349, No. 17.

Tian et al., "Toll-like receptor 9-dependent activation by DNA-containing immune complexes is mediated by HMGB1 and RAGE," Nat Immunol, May 2007, pp. 487-496, vol. 8, No. 5.

Vogl et al., "Mrp8 and Mrp14 are endogenous activators of Toll-like receptor 4, promoting lethal, endotoxin-induced shock," Nat. Med., Sep. 2007, pp. 1042-1049, vol. 13, No. 9.

Wang et al., "Abrogation of bleomycin-induced epithelial apoptosis and lung fibrosis by captopril or by a caspase inhibitor," Am. J. Physiol. Lung Cell. Mol. Physiol., 2000, pp. L143-L151, vol. 279.

Wang et al., "Induction of secondary apoptosis, inflammation, and lung fibrosis after intratracheal instillation of apoptotic cells in rats," Am J Physiol Lung Cell Mol Physiol, Apr. 2006, pp. L695-L702, vol. 290.

Watanabe et al., "Activation of the IL-1β-Processing Inflammasome is Involved in Contact Hypersensitivity," J Invest Dermatol, 2007, pp. 1956-1963, vol. 127.

Wright et al., "Mononuclear Phagocyte Xanthine Oxidoreductase Contributes to Cytokine-Induced Acute Lung Injury," Am J Respiratory Cell and Mole Biol, 2004, pp. 479-490, vol. 30, No. 4.

Wu et al., "Hyperuricemia and urate nephropathy in urate oxidase-deficient mice," Proc. Natl. Acad. Sci. USA, Jan. 1994, 742-746, vol. 91.

Yu et al., "HMGB1 Signals Through Toll-Like Receptor (TLR) 4 and TLR2," Shock, Aug. 2006, pp. 174-179, vol. 26, No. 2.

Zedler et al., "The impact of endogenous triggers on trauma-associated inflammation," Curr. Opin. Crit. Care, 2006, pp. 595-601, vol. 12.

\* cited by examiner

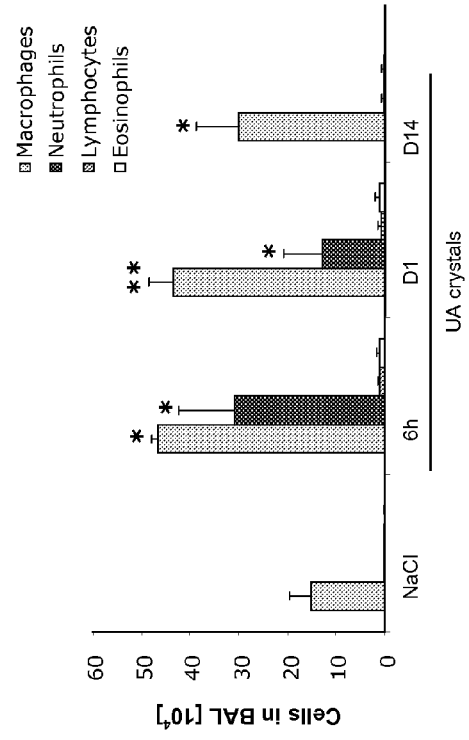
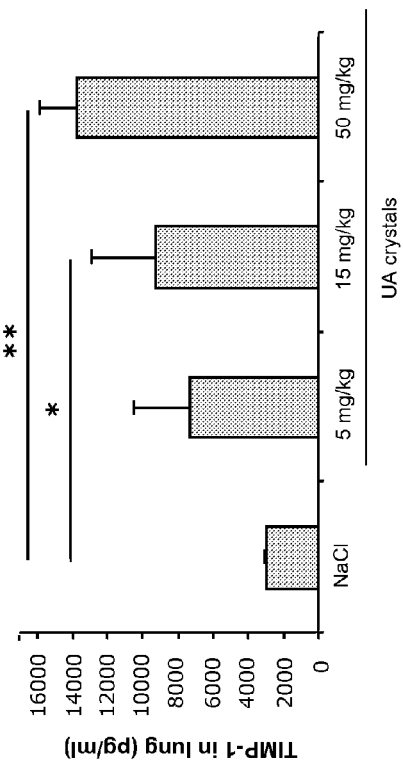
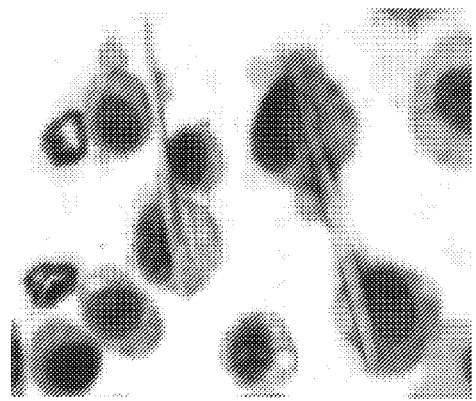
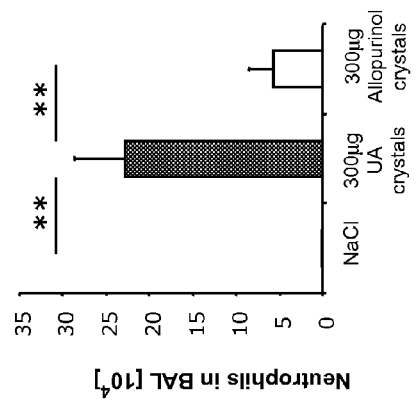
FIGURE 5A
FIGURE 5B
FIGURE 5C
FIGURE 5D

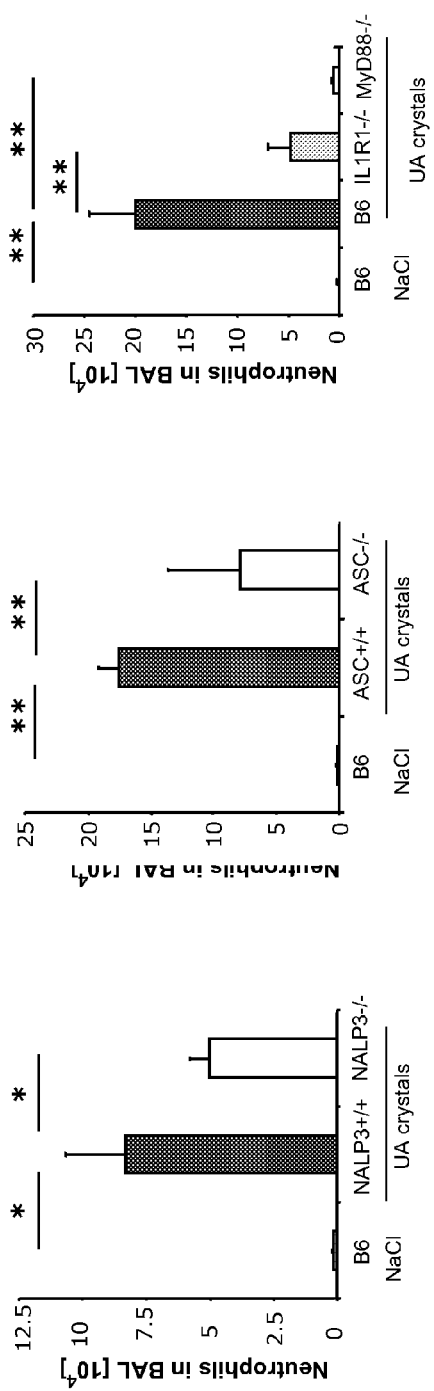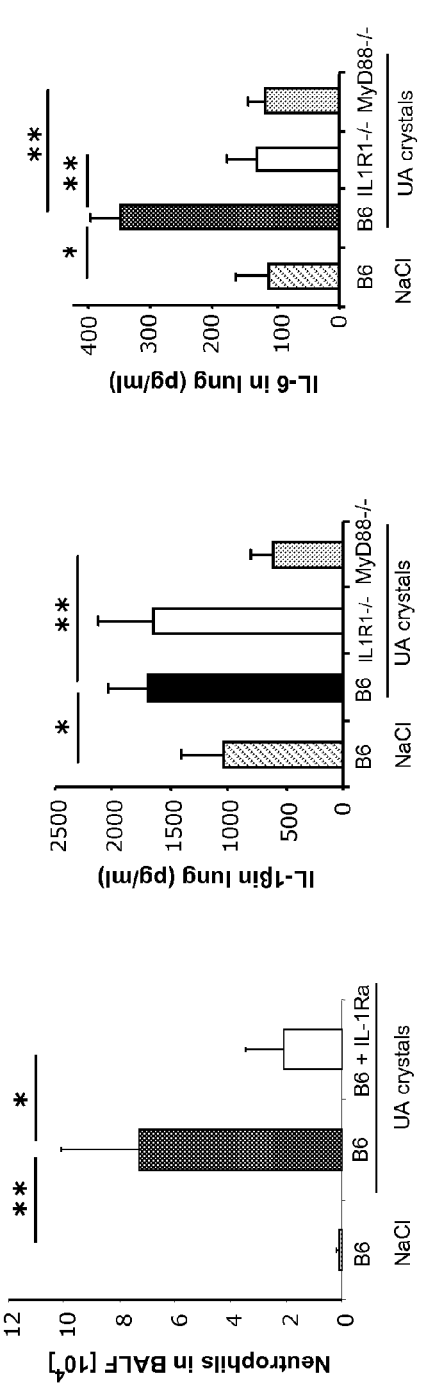
FIGURE 6A FIGURE 6B FIGURE 6C
FIGURE 6D FIGURE 6E FIGURE 6F

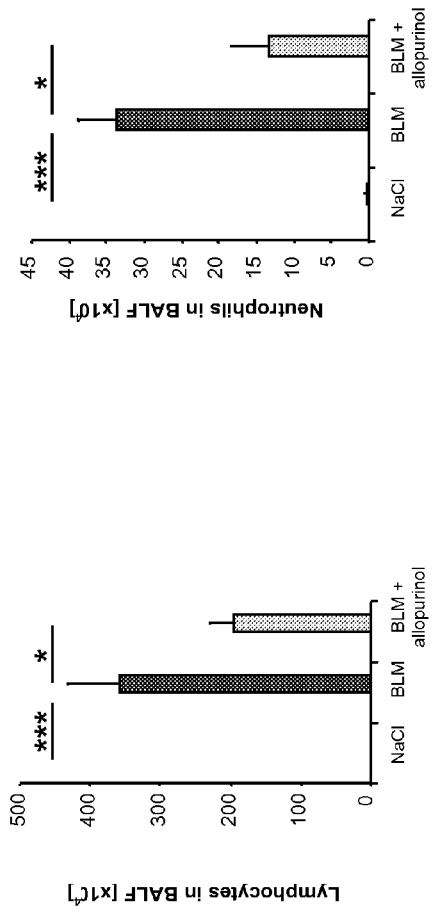
FIGURE 15A
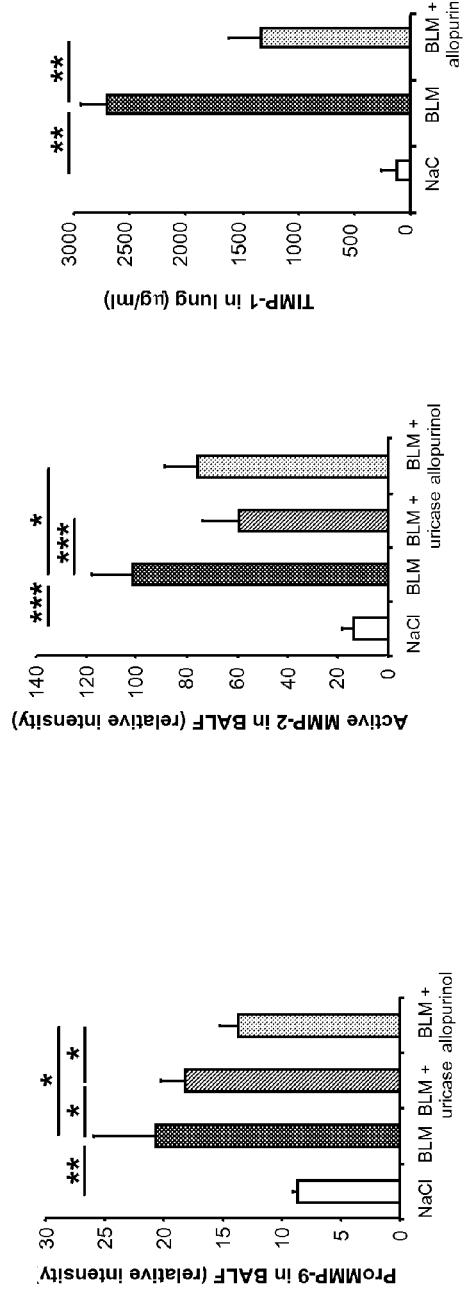
FIGURE 15C
FIGURE 15B

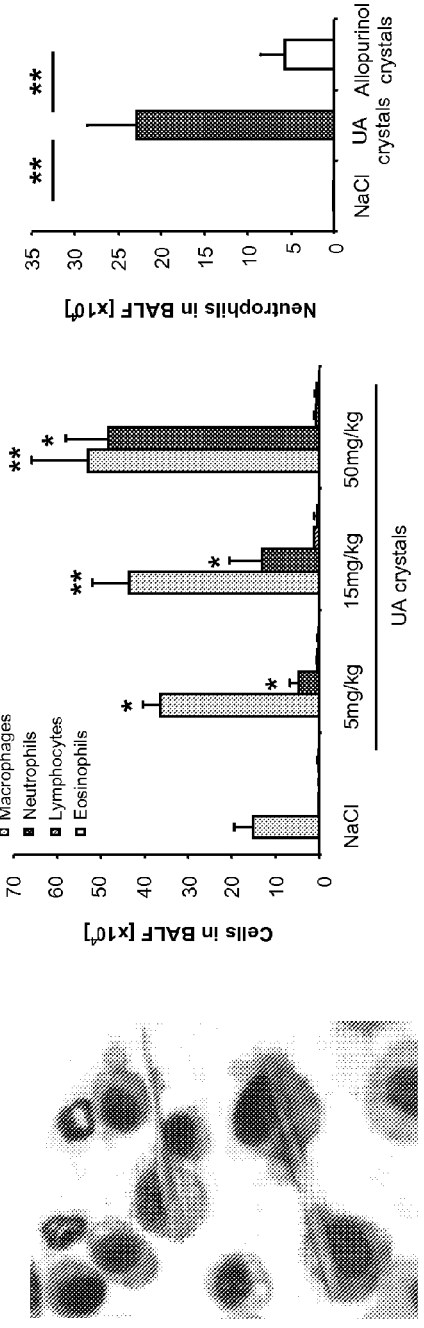
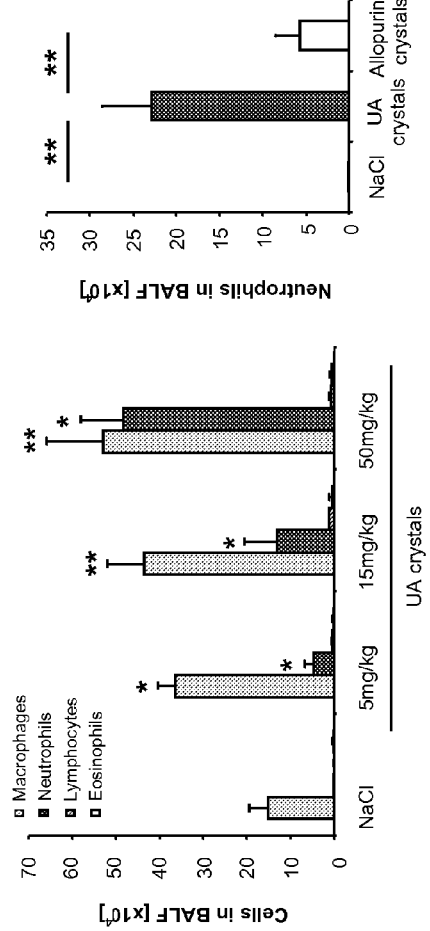
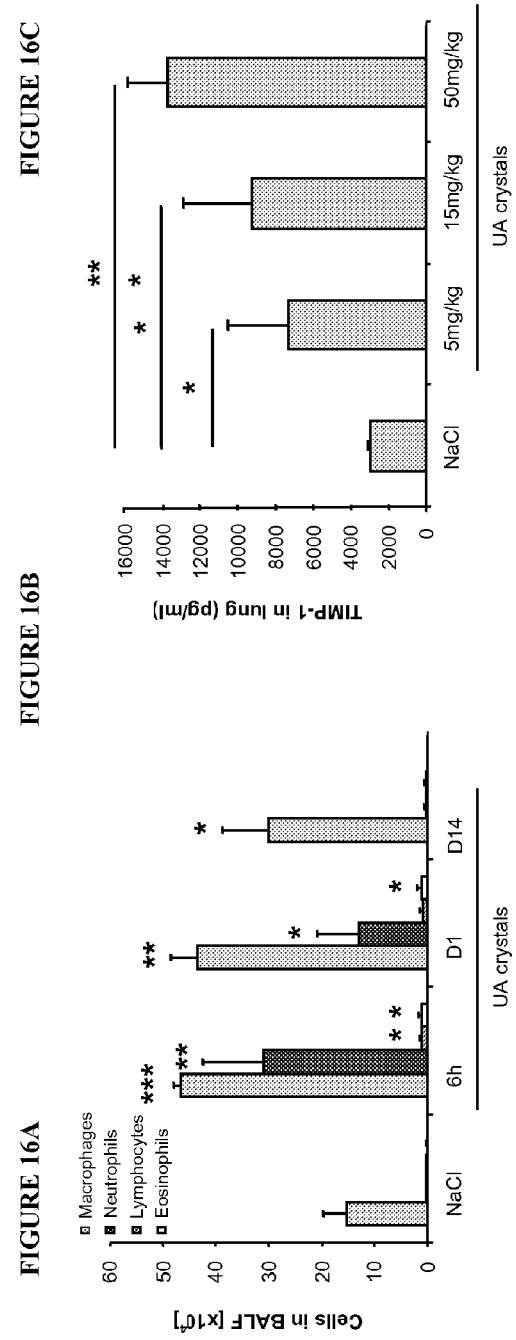
FIGURE 16A, FIGURE 16B, FIGURE 16C, FIGURE 16D, FIGURE 16E

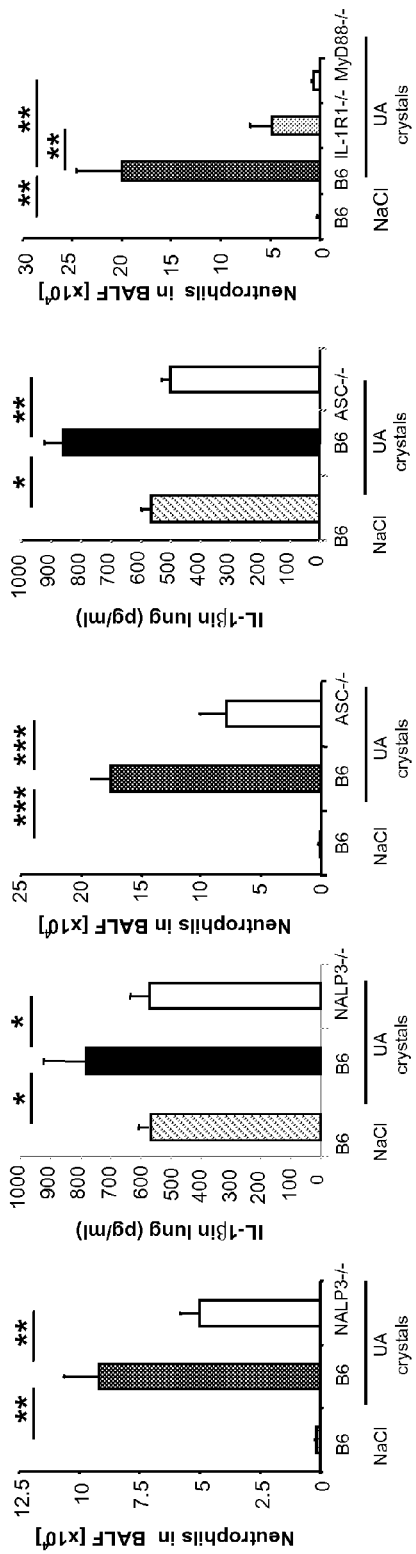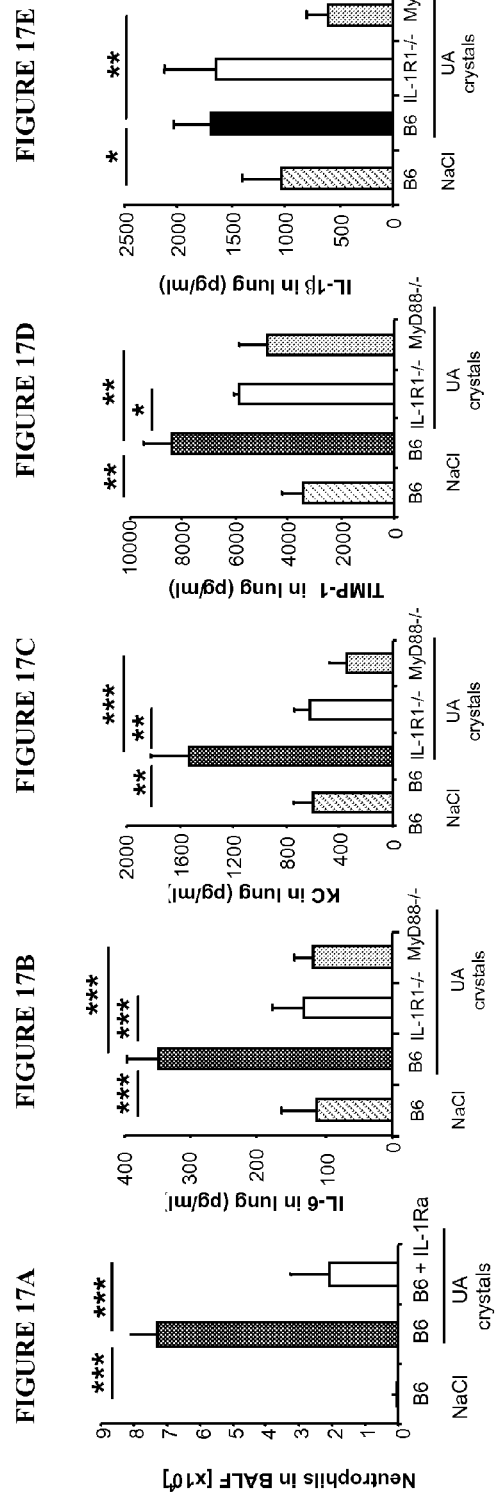
FIGURE 17A FIGURE 17B FIGURE 17C FIGURE 17D FIGURE 17E
FIGURE 17F FIGURE 17G FIGURE 17H FIGURE 17I FIGURE 17J

METHOD FOR THE PREVENTING AND/OR TREATING IL-1 BETA LUNG PATHOLOGY IN MAMMALS BY ADMINISTERING A URIC ACID REDUCING COMPOUND

This application is a U.S. National Stage application of PCT/EP2009/062159, filed Sept. 18, 2009, which claims priority to European Patent Application No. 083055657, filed Sept. 18, 2008, each and all of which are incorporated herein by reference in their entirety.

The present invention is directed to the use of a compound capable of reducing the uric acid level in a mammal for the prevention and/or the treatment of IL-1β driven lung pathology, particularly to treat lung inflammation such as chronic fibrosis, CPOD and interstitial fibrosis and other IL-1β driven lung pathologies including those of autoimmune origin. Preferred compounds capable of reducing the uric acid level are selected from the group consisting of xanthine oxidase inhibitors, such as allopurinol, recombinant enzyme uricase and uricosuric compound capable of enhancing uric acid excretion, such as probenecid. The invention further relates to a method for identifying in vitro whether a patient presents an IL-1β driven lung pathology or is at risk to develop an IL-1β driven lung pathology, or for the screening of a compound for treating an IL-1β driven lung pathology in a patient in need thereof.

Microbial components and cell damage represent danger signals and trigger innate immunity resulting in inflammation and repair (4). Dying cells release danger signals that alert the immune system and stimulate innate and adaptive immunity (5,6). Danger signals released from dying cells are recognized at the cell level via membrane receptors such as TLRs (7,8,9,39) or cytosolic receptors such as NLRs (10-14,36). Nucleic acids from injured cells are rapidly degraded and the purines are converted into uric acid. Uric acid, a product of purine catabolism, was identified in dying cells inducing the maturation and antigen presentation function of dendritic cells (16). Large amounts of uric acid are produced from injured tissue in vivo after tumor chemotherapy leading to hyperuricemia (17). At high local concentration uric acid precipitates and forms crystals which cause inflammation as observed in clinical gout (57). Uric acid crystals activate the NALP3 inflammasome containing caspase-1 resulting in the production of active interleukin (IL)-1β (10).

Figure 9:
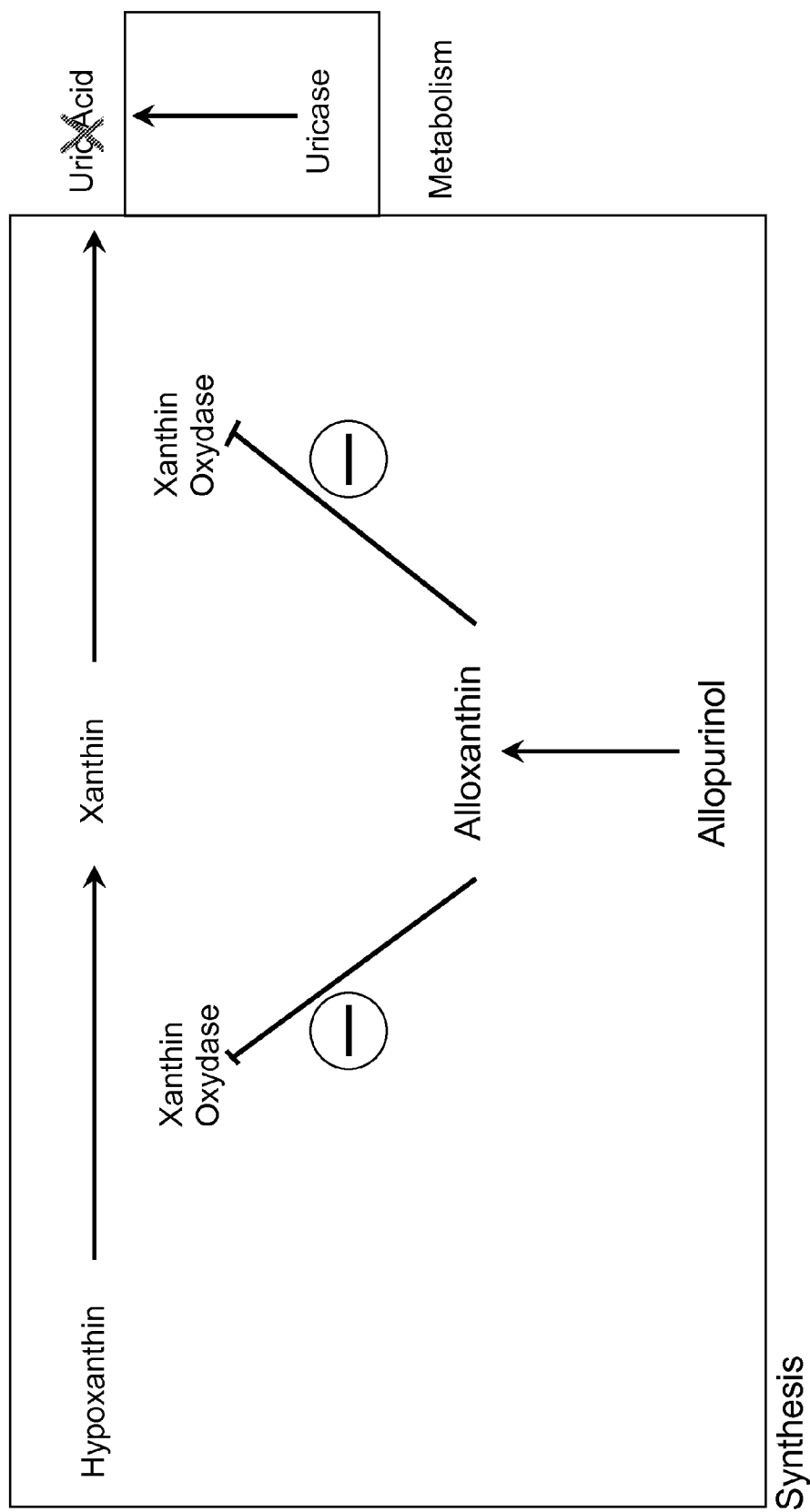
Figure 10B:
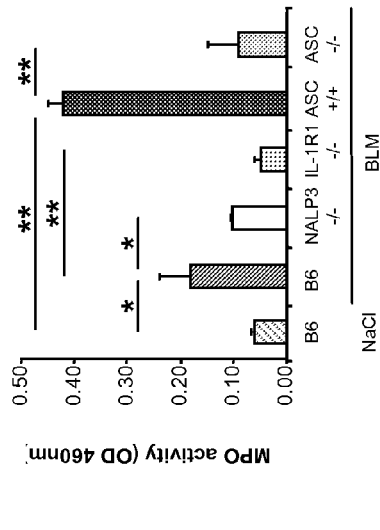
Figure 10D:
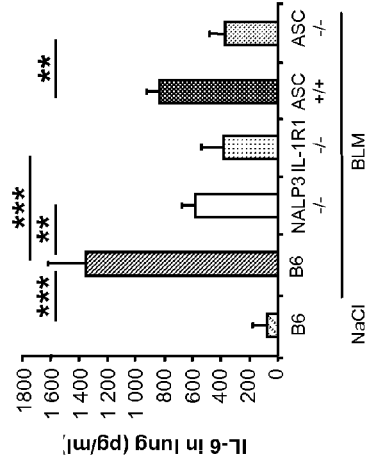
Figure 10A:
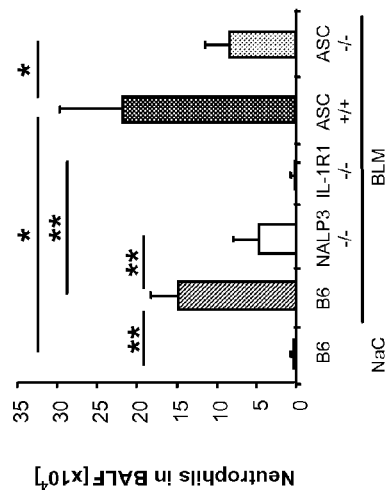
Figure 10C:
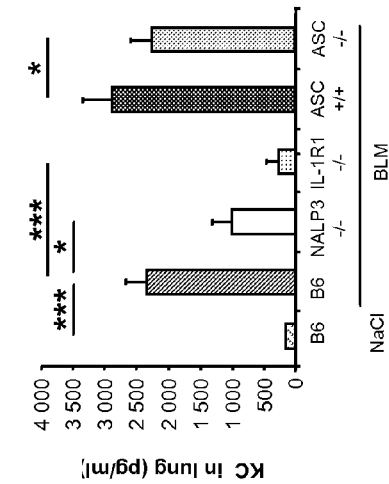
Figure 10F:
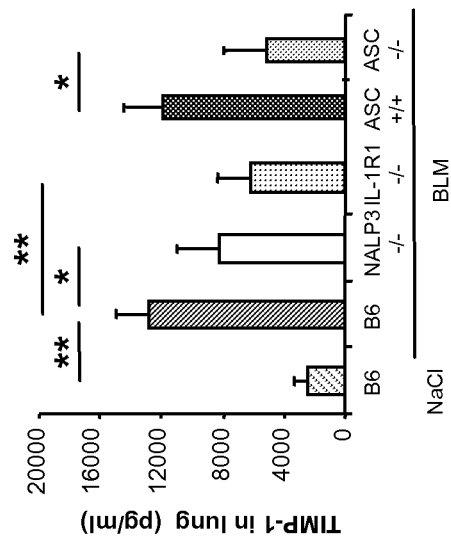
Figure 10E:
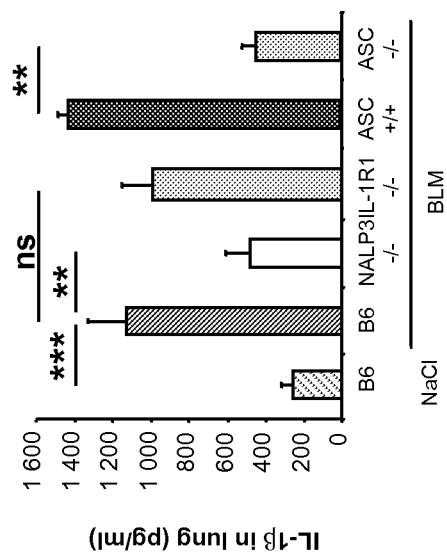
Figure 11C:
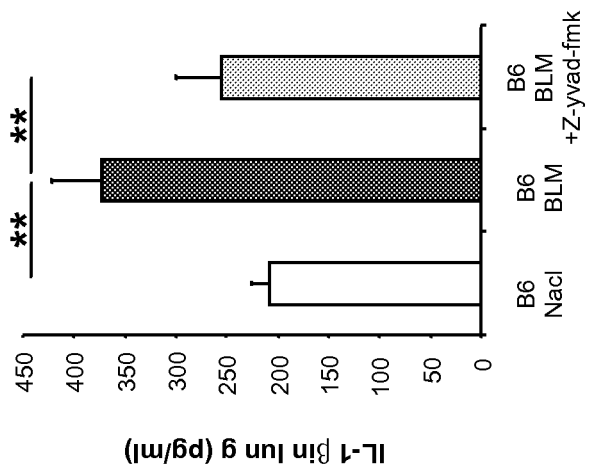
Figure 11B:
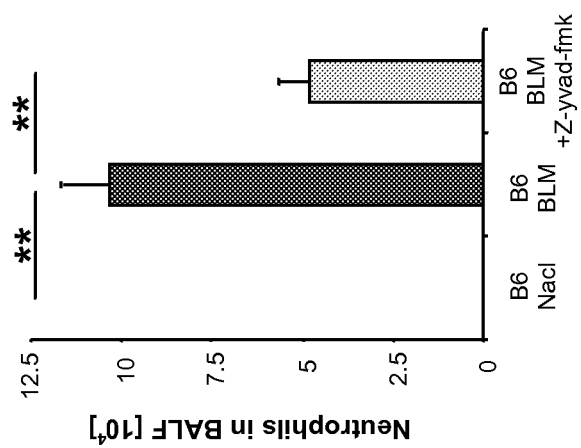
Figure 11A:
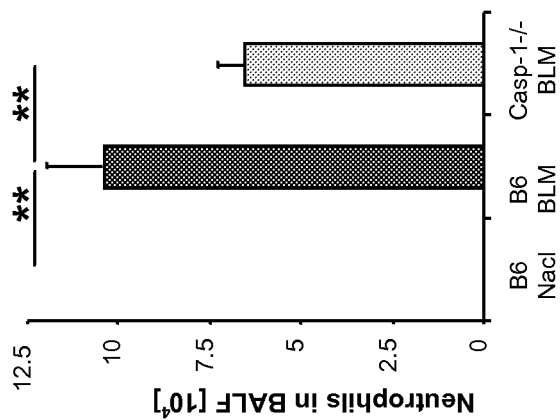

Hyperuricemic syndromes including gout can be effectively treated by inhibiting uric acid production, enhancing the degradation or urinary excretion (see the scheme of FIG. 9 which shows the purine metabolism).

Figure 7:
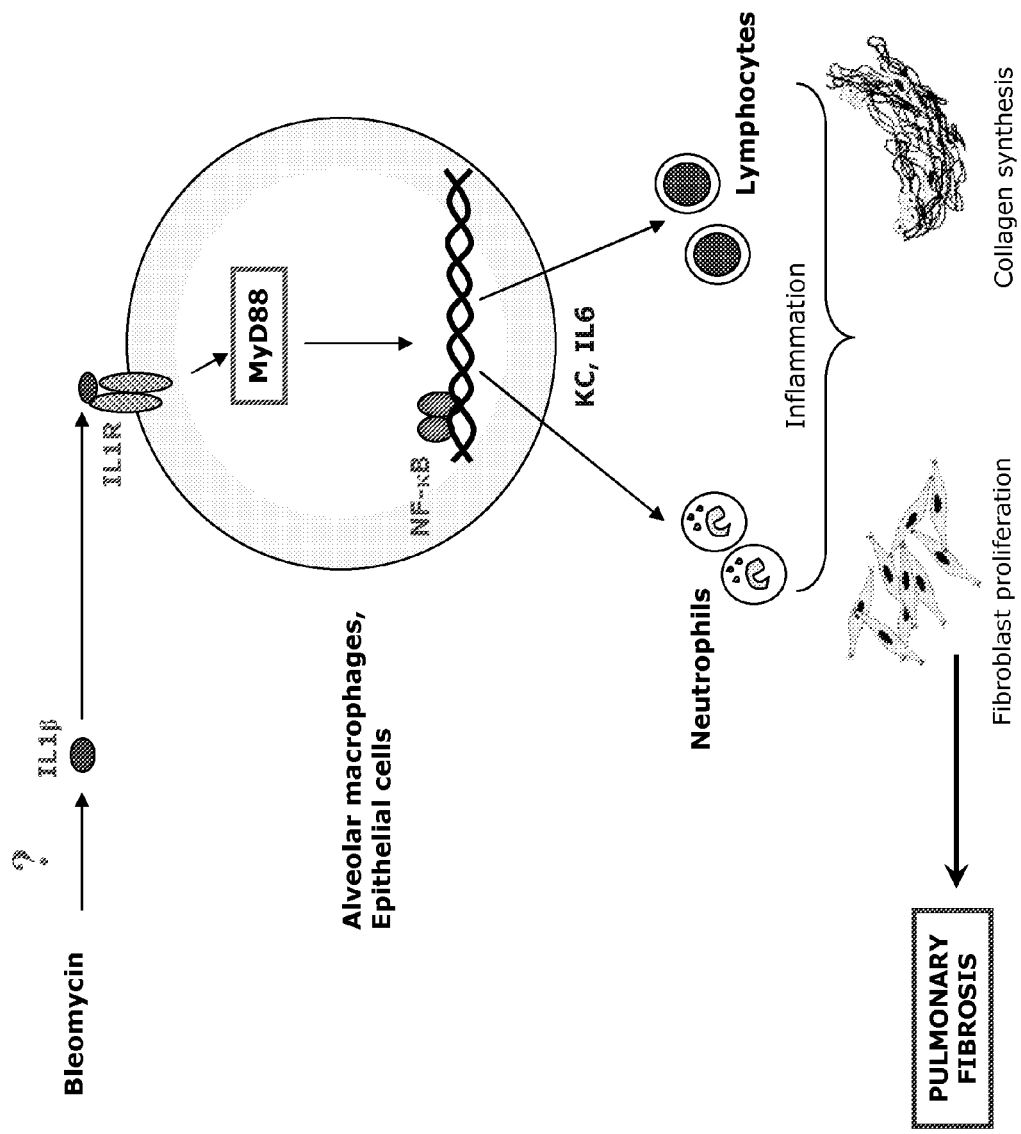

Interstitial pulmonary fibrosis is a chronic disease with recurrent episodes of acute lung injury which often leads respiratory failure with death. Importantly no effective therapy is available (1). The cause of the recurrent lung inflammation resulting in interstitial pulmonary fibrosis is mostly unknown. However, chronic airways irritation by pollutants, irradiation or tumor chemotherapy with bleomycin may cause similar fibrotic lung pathology. Bleomycin in experimental settings causes oxidative damage and cell death leading to lung inflammation and fibrosis which resembles interstitial pulmonary fibrosis (2,38). In this experimental model, it has been demonstrated that inflammation, repair and fibrosis are dependent on IL-1β production and IL-1R1/MyD88 signaling, and activation of the inflammasome complex is required to bleomycin-induced inflammation (3). These published findings are summarized in FIG. 1 and are presented schematically in FIG. 7.

Thus, it remains desirable to understand how IL-1β is produced in order to provide a method for the prevention and/or the treatment of lung inflammation and lung fibrosis. This is the object of the present invention.

The inventors report here that bleomycin-induced inflammation depends on the activation of the NALP3 inflammasome. They have demonstrated here that uric acid is locally produced in the lung upon tissue injury and causes inflammation and fibrosis via the production of the inflammatory cytokine IL-1β. Uric acid crystals given by the intranasal route caused dose-dependent NALP3-IL-1R1 dependent inflammation (summarized in FIG. 8).

The metabolism of uric acid is well established and only relevant points are highlighted: Xanthine oxidase oxidizes hypoxanthin to xanthin and uric acid, which is degraded by uricase to allantoin which is eliminated by the kidney. In the kidney uric acid elimination is enhanced by inhibiting tubular reabsorption by blocking the organic anion transporter, URAT1.

For each cited mechanism which reduces to uric acid levels, inhibitors are well known by the person having ordinary skill in the art and some of them are in clinical use:
For example,
    Allopurinol is a xanthine oxidase inhibitor and reduces the formation of uric acid
    Recombinant uricase degrades uric acid and thereby reduced hyperuricemia
    Probenecid inhibits the tubular organic anion transporter and thereby augments renal elimination.

Therefore, therapeutic tools to decrease uric acid levels can be used to reduce injury-induced cell death and lung inflammation and lung fibrosis.

Indeed, surprisingly and importantly, the inventors have demonstrated that reduction of uric acid levels by the administration of the xanthine oxidase inhibitor, allopurinol, inhibited IL-1β production and lung inflammation. Additionally, reduction of uric acid levels by recombinant enzyme uricase had a comparable inhibitory effect on lung inflammation.

This is the first report to show that uric acid is critically involved in lung inflammation and lung fibrosis and the inventors present compelling evidence that reduction of uric acid inhibits IL-1β production and thereby lung inflammation and fibrosis.

Figure 8:
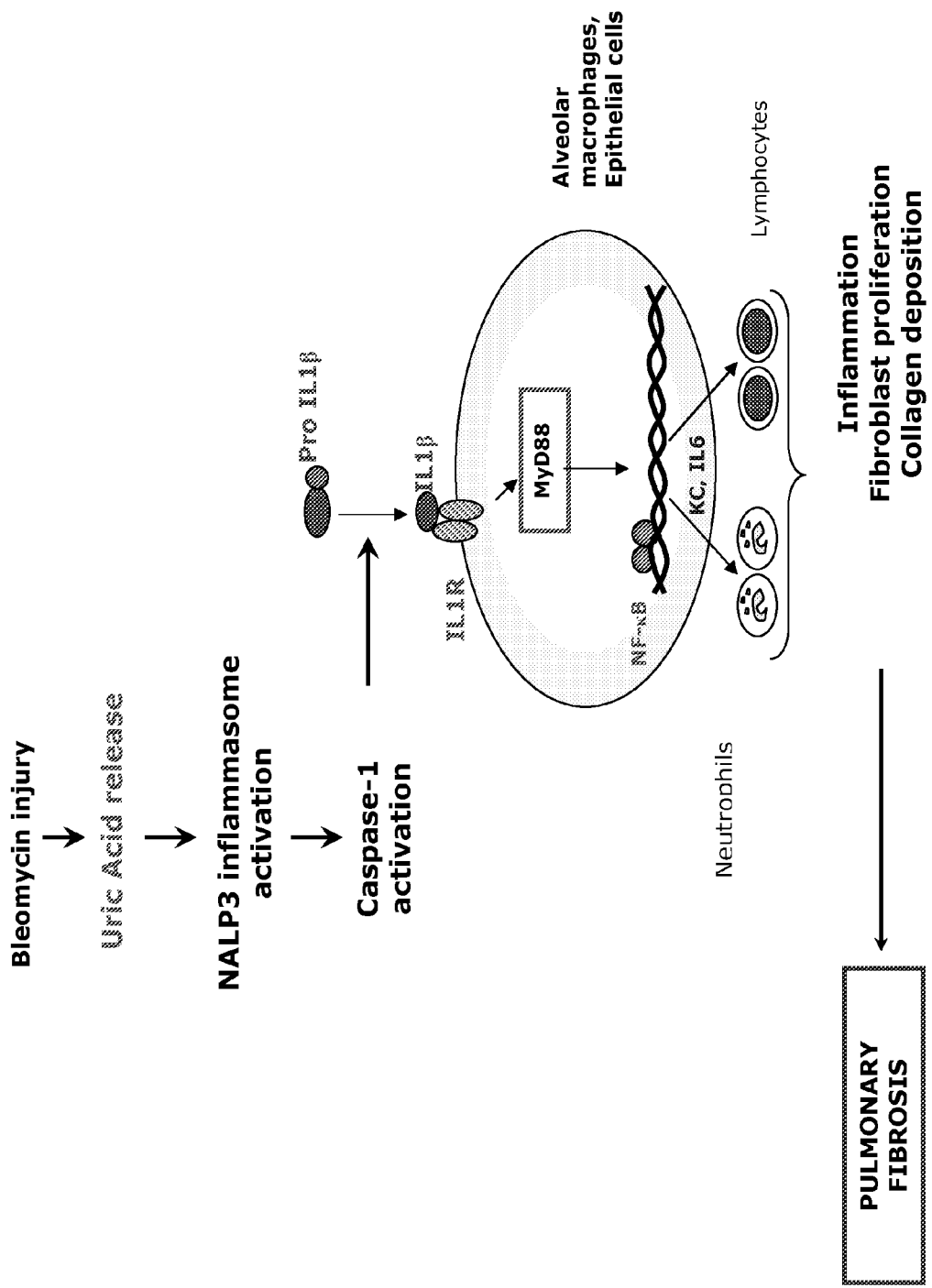

Based on the fact that cell/tissue injury and necrosis result in production of uric acid, the inventors hypothesized that uric acid crystals formed at the injury site might represent a key danger signal activating the inflammasome to release IL-1β causing inflammatory lung pathologies (shown schematically in FIG. 8).

The inventors have particularly demonstrated that uric acid is released upon bleomycin lung injury, and present compelling evidence that uric acid is critically involved in the activation of the NALP3 inflammasome resulting in caspase-1 activation which cleaves pro-IL-1β to mature IL-1β, which is then causing lung inflammation and fibrosis (FIG. 8).

The present invention relates to the use of a compound capable of reducing the uric acid level in a mammal for the preparation of a composition intended to the prevention and/or the treatment of IL-1β driven lung pathology.

The instant invention also comprises a method for the prevention and/or the treatment of IL-1β driven lung pathology in a mammal, especially humans, in need thereof by administering to such mammal an effective serum uric acid reducing amount of a therapeutical compound.

In a preferred embodiment, said IL-1β driven lung pathology is selected from the group consisting of lung inflammation, lung fibrosis such as chronic fibrosis, chronic obstructive pulmonary disease (COPD) and interstitial fibrosis and lung pathologies from autoimmune origin.

The preferred chronic obstructive pulmonary diseases are selected from the group consisting of asthma, bronchiectasis, chronic bronchitis, emphysema and any inflammatory lung disease including allergies.

In a more preferred embodiment, said IL-1β driven lung pathology is selected from the group consisting a lung inflammation leading to fibrosis and respiratory failure.

In another preferred embodiment, the compound capable of reducing the uric acid level is selected from the group consisting of:
- a xanthine oxidase inhibitor which is able to reduce uric acid concentrations through inhibiting uric acid production, or a pharmaceutically acceptable salt thereof;
- an uricase or urate oxydase, which catalyses the conversion of uric acid to the more readily excreted allantoin, or a functional fragment thereof; and
- an uricosuric compound or an inhibitor of the tubular organic anion transporter resulting to the augment renal elimination of uric acid which are capable of enhancing uric acid excretion, or a pharmaceutically acceptable salt thereof.

More preferred are xanthine oxidase inhibitor compounds selected from the group consisting of:
- allopurinol,
- pyrazolo[3,4-d]pyrimidines, structurally related with allopurinol. Gupta et al., Eur J Med. Chem. 2008; 43(4): 771-80, the complete disclosure of which is hereby incorporated by reference),
- azapropazone (the 3-dimethylamino-7-methyl-1,2-(n-propylmalonyl)-1,2-dihydro-1,2,4-benzotriazine dihydrate (see Thiele et al., Dec. 15, 1981, U.S. Pat. No. 4,305,942 the complete disclosure of which is hereby incorporated by reference),
- substituted thiazolopyrimidines (see U.S. Pat. No. 7,253,154, Yoshida et al., Aug. 7, 2007, the complete disclosure of which is hereby incorporated by reference),
- 1,2,4-triazole compound which may be substituted at the 1, 2 or 4 position with a substituted alkyl group and has aromatic rings at the 3 and 5 positions, a hydrate or a salt thereof (see U.S. Pat. No. 7,074,816, Nakamura et al., Jul. 11, 2006, the complete disclosure of which is hereby incorporated by reference), and
- 2-[3-cyano-4-(2-methylpropoxy)phenyl]-4-methylthiazole-5-carboxylic acid (Febuxostat, a nonpurine selective inhibitor of xanthine oxidase, which is a potential alternative to allopurinol for patients with hyperuricemia and gout (Becker, et al., N. Engl. J. Med., Volume 353:2450-2461, 2005, Number 23).

Also more preferred are purified uricase or urate oxydase, such as the urate oxydase extracted from *Aspergillus flavus* (known as Uricozyme®) preferably recombinant uricase or urate oxydase, such as rasburicase (recombinant urate oxydase from *Aspergillus flavus* expressed in *Saccharomyces cerevisiae*), or a functional fragment thereof.

More preferred are PEGylated uricases which are less antigenic than uricase and which can rapidly reduce serum uric acid concentrations (Bomalaski et al., Curr. Rheumatol. Rep 2004; 6:240-247). By PEGylated uricases or urate oxydases, it is intended to designate naturally occurring or recombinant uricase (urate oxidase) covalently coupled to poly(ethylene glycol) or poly(ethylene oxide) (both referred to as PEG), particularly wherein an average of 2 to 10 strands of PEG are conjugated to each uricase subunit, preferably wherein the PEG has an average molecular weight between about 5 kDa and 100 kDa. The resulting PEG-uricase conjugates were shown to be substantially non-immunogenic and to retain at least 75% of the uricolytic activity of the unmodified enzyme (see U.S. Pat. No. 6,576,235, published on Jun. 6, 2003, the complete disclosure of which is hereby incorporated by reference).

Also more preferred compounds capable of reducing the uric acid level are uricosuric compounds selected from the group consisting of:
- probenecid (4-[(dipropylamino)sulfonyl]benzoic acid, an anion transport inhibitor),
- benzbromarone (3,5-dibromo-4-hydroxyphenyl-2-ethyl-3-benzofuranyl ketone),
- sulfinpyrazone(1,2-diphenyl-4-(2-phenylsulfinylethyl) pyrazolidine-3,5-dione), and
- thromboxane synthetase inhibitors and/or thromboxane receptor antagonists (see U.S. Pat. No. 5,021,448, Piraino et al., Jun. 4, 1991, the complete disclosure of which is hereby incorporated by reference).

In a preferred embodiment, said composition is administered by intravenous injection, by intramuscular injection, by subcutaneous injection or orally.

The daily dosing of the active ingredient depends of the administration route chosen for the treatment. The dose will also depend on the amount of uric acid found in the biological sample in the patient to be tested. The skill person knows how to determine the best dosing in function of the age, the body weight and the data obtained relative to the serum, plasma or urine concentrations determined before and/or during the treatment.

For example, the prevention or the treatment of said IL-1β driven lung pathology, such as lung inflammation, lung fibrosis and lung pathologies from autoimmune origin, the active allopurinol or Febuxostat xanthine oxidase inhibitor ingredient can be administered to a subject suffering such a pathology for the duration of a few days in a daily dosage of up to about 1500 mg/d, preferably up to about 1000 mg/g, between about 40 and about 750 mg/d, and more preferably a daily dosage in the range of between 80 and 500 mg/d and between 120 and 400 mg/d.

For Example, for the prevention or the treatment of said IL-1β driven lung pathology, such as lung inflammation, lung fibrosis and lung pathologies from autoimmune origin, the active probenicid ingredient via oral route can be from 100 to 250 mg two times a day for about one week, then 200 to 500 mg two times a day for a few weeks.

For Example, for the prevention or the treatment of said IL-1β driven lung pathology, such as lung inflammation, lung fibrosis and lung pathologies from autoimmune origin, the active uricase ingredient can be administered to a subject suffering such a pathology for the duration of a few days in a daily dosage of up to about 2 mg/kg/d, preferably up to about 0.75, 0.50 and 0.35 mg/kg/d, preferably between about 0.10 and 0.30 mg/kg/d and, and more preferably a daily dosage in the range of between about 0.15 and 0.25 mg/kg/d, preferably by intravenous injection. For example the uricase ingredient can be administered as intravenous injections every 2 weeks at 4- and 8-mg doses or every 4 weeks at 8- or 12-mg doses for 12 weeks. Serum/plasma uricase concentrations, serum/plasma uric acid or urate, and, optionally, serum/plasma antibody anti-uricase can be determined during the treatment for better adjusting the treatment (seng Yue et al., The Journal of Clinical Pharmacology 2008; 48:708). The skill person knows how to determine the best doses in function of the age, the body weight and the data obtained relative to said serum/plasma concentrations.

In another aspect, the present invention is directed to a method for identifying in vitro whether a patient presents a IL-1β driven lung pathology or is at risk to develop a IL-1β driven lung pathology, wherein this method comprising the following steps of:

a) obtaining from the patient to be tested a biological fluid sample, particularly serum, plasma or urine sample;
b) determining the level of uric acid or urate; and
c) identifying whether said patient presents or is at risk to develop such a pathology by comparing the level of uric acid obtained for the patient to be tested with the level of uric acid or urate obtained in a blood sample for normal patients and/or for patients exhibiting a IL-1β driven lung pathology.

Preferably, the patient to be tested exhibits lung pathology symptom such as lung inflammation.

Preferably, the biological sample is a serum, plasma or urine sample.

When it is possible to obtain from the patient to be tested, bronchoalveolar lavage sample can be also used.

Preferably the determination of an uricemic control superior to 70 mg/L, more preferably 80, 90 and 100 mg/L of uric acid in serum or plasma sample is significant of an increased risk to develop or to present such a lung pathology.

Methods for the determination of uric acid in biological fluid sample, such as serum or plasma sample, are well known by the skill man. They can be for example enzymatic methods utilizing the enzyme uricase, methods based upon the ability of uric acid to reduce alkaline phosphotungstate, or miscellaneous chemical colorimetric methods. They are a wide variety of methods currently in use today for the uric acid or urate assay. For example, the uric acid assay kit ((Catalog #K608-100) from BioVision (BioVision Research Products, 980 Linda Vista Avenue, Mountain View, Calif. 94043 USA) or the Amplex® Red Uric Acid/Uricase Assay Kit (A22181) from Molecular Probes (29851 Willow Creek Road, Eugene, Oreg. 97402, USA)) wherein serum uric acid level can be measured using fluorometric or colorimetric methods can be cited.

In another aspect, the present invention is directed to a method for screening a compound for the treatment of lung pathology associated to IL-1β pathway ("IL-1β driven lung pathology"), wherein this method comprising the following steps of identifying whether said compound to be tested has a xanthine oxidase inhibitor, an uricase or urate oxydase activity, or is an uricosuric compound or an inhibitor of the tubular organic anion transporter resulting to the augment renal elimination of uric acid.

Preferably, said lung pathology associated to IL-1β pathway to be treated is selected from the group consisting of lung inflammation, lung fibrosis such as chronic fibrosis, chronic obstructive pulmonary disease (COPD) and interstitial fibrosis and lung pathologies from autoimmune origin.

More preferably, said lung pathology associated to IL-1β pathway to be treated is a lung inflammation leading to fibrosis and respiratory failure.

Other characteristics and advantages of the invention appear in the continuation of the description with the examples and the figures whose legends are represented below.

FIGURES LEGEND

FIGS. 1A-1F: Bleomycin induced lung inflammation and fibrosis depends on IL-1β

FIGS. 2A-2F: Bleomycin induced IL-1β production in the lung depends on inflammasome activation FIGS. 3A-3E: Uric acid is produced in the lung upon bleomycin administration and inhibition of uric acid synthesis by allopurinol prevents lung inflammation FIGS. 4A-4C: Uric acid degradation by uricase inhibits bleomycin induced lung inflammation FIGS. 5A-5D: Exogenous uric acid crystals cause inflammation and IL-1β production FIGS. 6A-6H: Exogenous uric acid crystals induced inflammation depends on the NALP3 inflammasome activation FIG. 7: Schematic summary of our published data on bleomycin induced IL-1β production, inflammation and fibrosis FIG. 8: Novel data: Pulmonary uric acid production upon bleomycin lung injury activating the NALP3 inflammasome with the production of IL-1β resulting in lung inflammation and fibrosis FIG. 9: Synthesis and metabolism of uric acid: Reduction of uric acid by allopurinol and related xanthine oxidase inhibitors and uricase.

FIGS. 10A-10F: Bleomycin-induced pulmonary inflammation and remodeling are dependent on NALP3 and ASC proteins (A) Neutrophil counts in BALF, (B) MPO activity in lung homogenates, (C) KC, (D) IL-6, (E) IL-1β and (F) TIMP-1 concentrations in lung homogenates, 24 h after bleomycin (BLM, 10 mg/kg) intranasal instillation (i.n.) installation of wild-type, NALP3, IL-1R1 or ASC deficient mice. In this experiment, ASC−/−, backcrossed only 4 times were compared to their ASC+/+ littermate. These data were reproduced with ASC−/− backcrossed on 10 generations onto a C57BL/6. Data are representative of 4 independent experiments and are expressed as mean values±SD (n=5 mice per group; *, $p<0.05$; , $p<0.01$; *, $p<0.001$; ns, non significant).

FIGS. 11A-11E: Bleomycin-induced inflammation is dependent on caspase-1 Neutrophil counts in BALF, 24 h after BLM (10 mg/kg) i.n. instillation of wild-type mice or caspase-1 (Casp-1) deficient mice (A). Neutrophil counts in BALF (B), IL-1β (C), KC (D) and TIMP-1 (E) concentrations in lung homogenates 24 h after BLM (10 mg/kg) i.n. instillation of wild-type mice injected i.p. with vehicle or an inhibitor of Casp-1 Z-yvad-fmk (10 mg/kg) just before, 4 and 8 h thereafter BLM administration. Data are representative of 3 independent experiments and are expressed as mean values.

FIGS. 12A-12D: Late inflammation and remodeling depend on the NALP3 inflammasome Late inflammation and tissue remodeling were evaluated in wild-type and deficient mice 14 days after administrated with bleomycin (5 mg/kg, i.n.). (A) Late inflammation measured as lymphocytes in the BALF. (B) Pro-MMP-9 (100 Kd), Pro-MMP-2 (71 Kd) and active MMP-2 (65 Kd) gelatinase activities, were analyzed by zymography in the BALF. (C) TIMP-1 as indicator of a fibrotic process was measured in the lungs by ELISA. (D) Total collagen in the lung was analyzed by Sircol assay. Data represent mean values±SD from 3 independent experiments (n=6 mice per group; *, $p<0.05$; , $p<0.01$, *, $p<0.001$; ns, not significant).

FIGS. 13A-13G: Bleomycin-induced inflammation is reduced by uric acid synthesis inhibition (A) Uric acid levels in BALF of mice 6 h after saline or bleomycin (BLM intranasal instillation (10 mg/kg). (B) Uric acid levels in lung of mice 24 h after saline or BLM treatment. Mice received a subcutaneous (s.c.) injection of vehicle or allopurinol (25 mg/kg) before BLM instillation and 6 and 9 h after. (C) Total cell and (D) neutrophil counts in BALF after s.c. injection of vehicle or allopurinol and saline or BLM instillation. KC (E), IL-1β production (F) in lung 24 h or TIMP-1 (G) production in lung homogenates 24 h after s.c.

injection of vehicle or allopurinol and BLM instillation. Data are representative of 3 independent experiments and are expressed as mean values±SD (n=6 mice per group; *, p<0.05; , p<0.01, *, p<0.001).

Figures 14A, 14B, 14C:
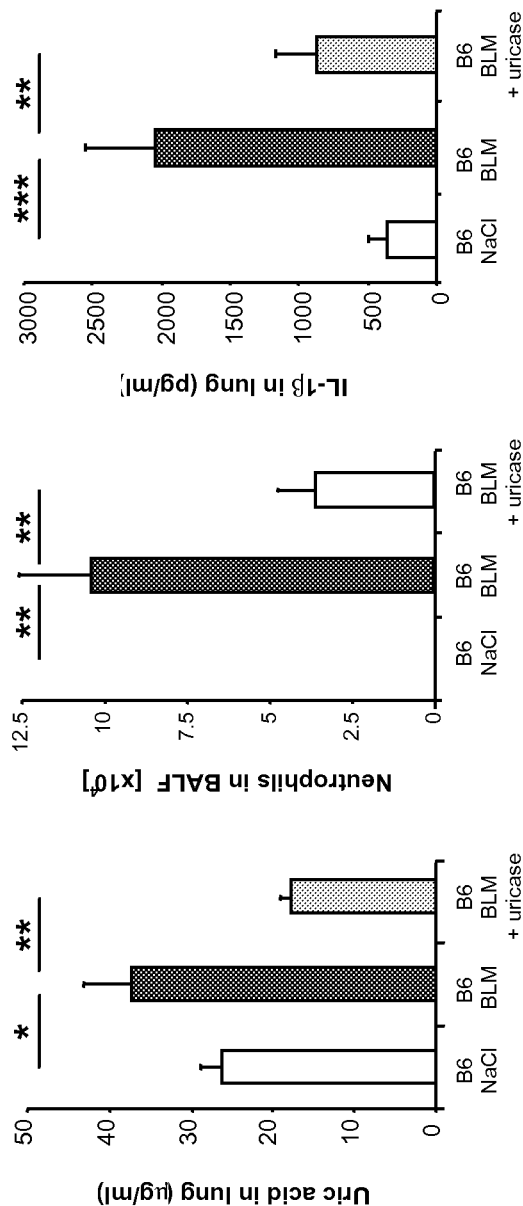

FIGS. 14A-14C: Bleomycin-induced inflammation is reduced by uric acid neutralisation Uric acid levels in lung (A), neutrophil counts in BALF (B) and IL-1 production in lung (C) 24 h after BLM instillation (10 mg/kg). Mice were injected i.p. with vehicle or uricase (0.2 mg/kg) just before instillation with BLM and 6 and 9 h thereafter. Data are representative of 4 independent experiments and are expressed as mean values±SD (n=6 mice per group; *, p<0.05; , p<0.01, *, p<0.001).

FIGS. 15A-15F: Bleomycin-induced repair and fibrosis are mediated by uric acid

Mice were injected at day 0 with allopurinol (15 mg/kg, s.c.), uricase (0.2 mg/kg, i.p.) or saline, at 0, 6 and 9 h after BLM instillation (5 mg/kg, i.n.) and every second days during 8 or 14 days to evaluate remodeling and fibrosis. (A) Late inflammation measured as lymphocytes and neutrophils in the BALF at day 8. (B) Pro-MMP-9 (100 Kd), Pro- and active MMP-2 (65 Kd) gelatinase activities, analyzed by zymography were upregulated in the BALF of vehicle treated mice but less in the BALF of allopurinol or uricase treated mice at day 14. (C) TIMP-1 as indicator of a fibrotic process was upregulated in the lungs 8 days after BLM administration of saline mice, but not in allopurinol treated mice. (D) Alpha1 (I) collagen I mRNA in lung was analyzed by real time quantitative polymerase chain reaction (PCR) amplification after uricase or allopurinol treatment 14 days after BLM administration. Data represent mean values±SD from 3 independent experiments (n=6 mice per group; *, p<0.05; , p<0.01, *, p<0.001; ns, not significant). (E) Lung microscopic sections showed extensive fibrotic areas at day 14 with collagen deposition in wild-type mice treated with BLM in comparison to saline control mice. Fibrosis induced by BLM was significantly reduced by allopurinol. Chromotrope Aniline Blue (CAB) staining, 20× and 200× magnification. (F) The lesions induced by bleomycin were assessed semi-quantitatively by two pathologists as described (see Materials and methods). Lung destruction, thickening of the alveolar septae and fibrosis were reduced in mice treated with uricase or allopurinol. Results are expressed as mean lung fibrotic score±SD. Data represent mean values±SD from 3 independent experiments (n=6 mice per group).

FIGS. 16A-16E: Exogenous uric acid crystals cause acute lung inflammation and remodeling (A) Alveolar macrophages (AM) uptake of uric acid (UA) crystals 6 h after UA crystals instillation (15 mg/kg i.n). (B) Dose response of UA crystals-induced cell recruitment in BALF. (C) Neutrophil counts in BALF 6 h after UA or allopurinol crystals instillation (15 mg/kg i.n). (D) Kinetics of cell recruitment in BALF upon UA crystals instillation (15 mg/kg i.n.). (E) TIMP-1 in lung homogenates after i.n. administration of increasing doses of UA crystals. Data are representative of 3 independent experiments and are expressed as mean values±SD (n=4 mice per group; *, p<0.05; , p<0.01; *, p<0.001).

FIGS. 17A-17J: Pulmonary inflammation upon exogenous uric acid (UA) crystals is dependent upon NALP3 inflammasome and IL-1R1/MyD88 pathways Neutrophil counts in BALF from mice deficient for (A) NALP3, (C) ASC, (E) IL-1R1 or MyD88 and (F) in BALF from wild-type mice pretreated i.p. with anakinra (10 mg/kg), 6 h after exogenous UA crystals instillation (15 mg/kg). IL-1β dosages in lung homogenates, 6 h after exogenous UA crystals administration for (B) NALP3, (D) ASC, (F) IL-1R1 or MyD88 deficient mice in comparison to wild-type mice. (G) IL-6, (H) KC, (I) TIMP-1 and IL-1β dosages in lung homogenates, 6 h after exogenous UA crystals administration of wild-type or IL-1R1 or MyD88 gene deficient mice. Data are representative of 3 independent experiments and are expressed as mean values±SD (n=4 mice per group; *, p<0.05; , p<0.01; *, p<0.001).

FIGS. 18A-18D: Pulmonary inflammation upon exogenous uric acid (UA) crystals is independent of IL-18R but requires TLR2 or TLR4 for optimal inflammation.

(A) Neutrophils count in BALF and (B) IL-1β in lung homogenates of TLR2, TLR4 or TLR2/TLR4 deficient mice. (C) Neutrophil counts in BALF and (D) IL-1β in lung homogenates of IL-18R deficient mice. Mice were sacrificed 6 h after exogenous UA crystals instillation (15 mg/kg). Data are representative of 3 independent experiments and are expressed as mean values±SD (n=4 mice per group; *, p<0.05; , p<0.01; *, p<0.001; ns, non significant).

Figure 19:
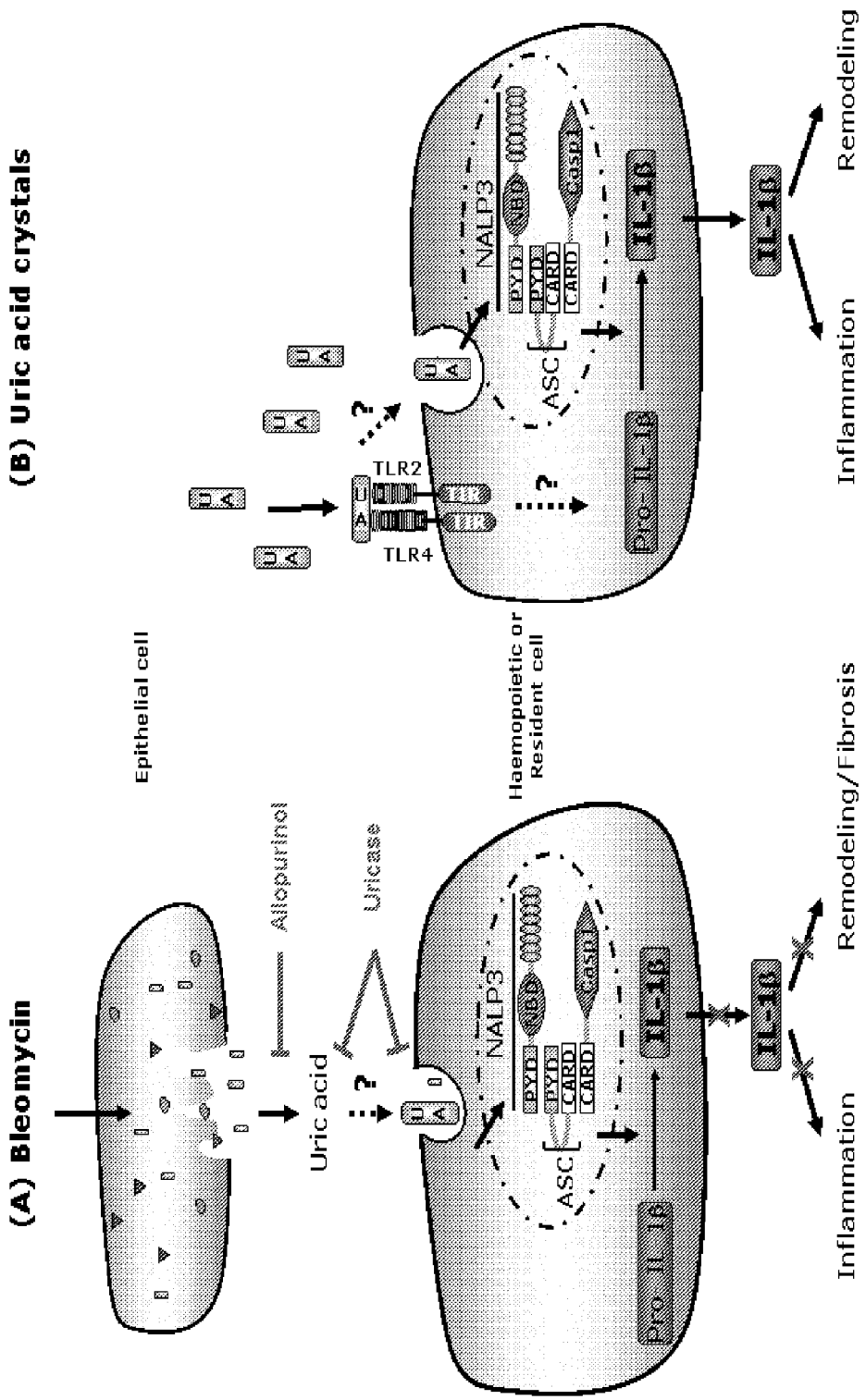

FIGS. 19A and 19B: Schematic diagram illustrating the specific cascades and signaling pathways after bleomycin-induced lung injury (A) or after lung exposition to exogenous uric acid crystals (B).

(A) We show first that bleomycin-induced injury of lung cells, probably epithelial cells leads to lung IL-1β production, inflammation and remodeling which are dependent on the NALP3 receptor, the ASC adaptor and the Casp-1 effector molecules. Second, we demonstrate that pulmonary bleomycin administration induces the release of uric acid in the lung which represents a danger/stress signal likely generated from dying lung cells upon injury. The activation of a NALP3 protein leads to the recruitment of ASC and Casp-1 known to interact via PYR-PYR and CARD-CARD homotypic interactions. Local concentration increase probably induces uric acid crystallization. In vivo treatment with the xanthine oxidase inhibitor allopurinol, which impairs uric acid synthesis, or treatment with uricase, which rapidly degrades uric acid into soluble allantoin, prevents uric acid concentration increase in the lung upon bleomycin administration and yields decreases in IL-1β production, inflammation, remodeling and fibrosis.

(B) Lung exposition to exogenous uric acid crystals induces inflammation and remodeling typical of evolution toward fibrosis with TIMP-1 accumulation. Uric acid crystals induced IL-1β production, inflammation and remodeling are dependent on the NALP3 inflammasome. The presence of TLR2 or TLR4 is necessary for IL-1β production and cellular influx. TLR2 and/or TLR4 may be involved in crystal-induced production of pro-IL-1β or in uric acid crystals uptake by alveolar macrophages and/or resident cells.

EXAMPLE 1

Materials and Methods

Mice

Mice are purchased from commercial sources or obtained from their laboratories of origin and bred as previously described (3) and (40). All animal experiments complied with the French Government's ethical and animal experiment regulations. The following mice deficient for MyD88 (19), IL-1R1 (20), IL-18R (21), Casp-1 (22), TLR4 (23), TLR2 (24), NALP3 (10) or ASC (25) were used in this study. MyD88−/−, Casp-1−/−, TLR2−/−, ASC−/− TLR4−/−, double deficient TLR2−/−TLR4−/− and IL-18R were backcrossed 10 times on the wild type C57BL/6 genetic background except in FIG. 1 where ASC−/−, backcrossed only 4 times were compared to their ASC+/+ littermate. IL-1R1−/− mice were backcrossed 7 times and NALP3−/− mice were directly generated on the C57BL/6 genetic background. All mice, including control C57BL/6, were bred in our animal facility at the Transgenose Institute (CNRS, Orleans). For experiments, adult (6-10 weeks old) animals were kept in sterile isolated ventilated cages. All animal experiments complied with the French Government's ethical and animal experiment regulations.

Bleomycin-, Uric Acid or Allopurinol Crystals-Induced Inflammation

Bleomycin sulfate (200-300 µg or 10-15 mg/kg) from Bellon Laboratories (Montrouge, France) in saline, uric acid or allopurinol crystals (100-1000 µg or 5-50 mg/kg) in saline or saline alone are given through the airways by nasal instillation in a volume of 40 µt, under light ketamine-xylasine anaesthesia. The number of cells, chemokines, cytokines and TIMP-1 in the bronchoalveolar space and in the lung were evaluated as described (3). Allopurinol (Sigma-Aldrich) was injected at 500 µg or 25 mg/kg subcutaneously in 0.1-ml sterile NaCl, uricase (Fasturtec, Sanofi Synthelabo) given at 4 µg or 0.2 mg/kg by nasal instillation in 40 µt, at the time of bleomycin administration, at 6 and 9 h. In some experiments, the IL-1Ra (Anakinra, Amgen) was injected at 200 µg or 10 mg/kg subcutaneously in 0.1-ml sterile NaCl, at the time of MSU crystals administration, at 2 and 4 h.

Uric Acid or Allopurinol Crystals Preparation

Uric acid or allopurinol crystals were obtained by dissolving 1.68 mg of powder in 0.01 M NaOH preheated to 70° C. and added as required to maintain pH between 7.1 and 7.2. The solution was filtered and incubated at room temperature under slowly and continuously agitation, until crystals have formed. Crystals were washed twice with ethanol 100%, dried, autoclaved and kept sterile. The weight of dry crystals was determined under sterile conditions, crystals are resuspended in PBS by sonication and examined under phase microscopy.

Lung Inflammation Model Experimental Design

Bleomycin sulfate (10 mg/kg) from Bellon Laboratories, uric acid or allopurinol crystals (5-50 mg/kg) in saline or vehicle alone were administered by intranasal instillation under light ketamine-xylasine anesthesia, and BAL and lung tissue assayed after 6 h (for uric acid crystal) or 24 h (for bleomycin) for markers of inflammation including cell recruitment and in particular neutrophil influx, chemokine and cytokine levels including KC, IL-6 and IL-1β and 14 days later for markers of tissue remodeling such as gelatinases MMP9 and MMP2 and their inhibitor TIMP-1. Allopurinol (Sigma-Aldrich) was injected at 25 mg/kg subcutaneously and uricase (Fasturtec, Sanofi Synthelabo) was given at 0.2 mg/kg intraperitoneally or intranasally in some experiments with similar efficacy. IL-1Ra (Anakinra, Amgen) was injected at 10 mg/kg subcutaneously. Optimized doses of allopurinol or uricase were tested and repeated administrations were more effective than higher doses (data not shown).

Bronchoalveolar Lavage Fluid (BALF)

After incision of the trachea, a plastic cannula was inserted and airspaces were washed using 0.3 ml of PBS solution, heated to 37° C. The rib cage was then gently massaged to enable maximum cell collection. The fluid was collected by careful aspiration. This procedure was performed ten times and the recovery of the total lavage exceeded 95%. The samples collected were dispatched in 2 fractions: the first one (1 ml corresponding to the 2 first lavages) was used for mediator measurement and the second one for the cell determination (4 ml). The first fraction was centrifuged (600 g for 10 min) and supernatant was fractionated and kept at −80° C. until mediator determination. The cell pellet was then resuspended in 0.4 ml PBS and, pooled with the second fraction and maintained at 4° C. until cell determination.

Lung Homogenization

After BAL was performed, the whole lung removed and placed inside a microtube (Lysing matrix D, Q Bio Gene, Illkrich, France) with 1 ml of PBS, total lung tissue extract was prepared using a Fastprep® system (FP120, Q Bio Gene, Illkrich, France), the extract was then centrifuged and the supernatant stored at −80° C. before mediator measurement, MPO or collagen assay with Sircol Collagen Assay (France Biochem Division, France).

Myeloperoxidase Activity (MPO) in Lung

Lung tissue MPO activity was evaluated as described (3). In brief, the right heart ventricle was perfused with saline to flush the vascular content and lungs were frozen at −20° C. until use. Lung was homogenized by polytron, centrifuged and the supernatant was discarded. The pellets were resuspended in 1 mL PBS containing 0.5% hexadecyltrimethyl ammonium bromide (HTAB) and 5 mM ethylene-diamine tetra-acetic acid (EDTA). Following centrifugation, 50 µL of supernatants were placed in test tubes with 200 µL PBS-HTAB-EDTA, 2 mL Hanks' balanced salt solution (HBSS), 100 µL of o-dianisidine dihydrochloride (1.25 mg/mL), and 100 µL $H_2O_2$ 0.05%. After 15 min of incubation at 37° C. in an adequate form, the reaction was stopped with 100 µL $NaN_3$ 1%. The MPO activity was determined as absorbance at 460 nm against medium.

Cell Count and Determination

Total cell count was determined in BAL fluid using a particle counter (Z2 Coulter, Beckman Coulter). Differential cell counts were performed on cytospin preparations (Cytospin 3, Thermo Shandon) after staining with 4 min May-Grünwald stain (MG-1L, Sigma chemical, Saint Louis, USA) and 8 min in 95% Giemsa stain (GS-500, Sigma chemical, Saint Louis, USA). Differential cell counts were made on 100 cells using standard morphological criteria.

Mediator Measurements

IL-1β, KC, IL-6 and TIMP-1 levels in BAL fluid or lung homogenate were determined using ELISA assay kits according to manufacturer's instructions (Mouse DuoSet, R&D system, Minneapolis, USA). IL-1β ELISA assay kit (mouse IL-1β/IL-1F2) specific for natural and recombinant mouse IL-1β exhibited no cross-reactivity or interference with recombinant mouse IL-1α, IL-1ra, IL-1RI/Fc Chimera or IL-1RII/Fc Chimera (Mouse IL-1 specific polyclonal goat IgG and Monoclonal rat IgG1, clone #30311).

Uric Acid Measurement

Uric acid concentration was determined in bronchoalveolar lavages and lung homogenates using Amplex® Red Uric Acid/Uricase Assay Kit (Molecular Probe, Eugene). Briefly, uricase catalyzes the conversion of uric acid to allantoin, hydrogen peroxide ($H_2O_2$) and carbon dioxide. In the presence of horseradish peroxidase (HRP), $H_2O_2$ reacts stoichiometrically with Amplex Red reagent to generate the red-fluorescent oxidation product, resorufin, measured spectrophotometrically.

Zymographic Analysis of MMPs

MMP-2 and MMP-9 levels were determined by gelatin zymography. Briefly, non-reduced supernatant samples of BAL fluid (15 µl) and standards (161-0305, Bio-Rad, Hercule, USA) were loaded onto 7% polyacrylamide gels (wt/vol) incorporating 0.1% (wt/vol) gelatin substrate. The MMP in the gelatinolytic bands were evaluated using as references recombinant murine Pro-MMP-9 (100 Kd) and recombinant murine Pro-MMP-2 (72 Kd). Proteins were subjected to electrophoresis at 20-30 mA for 3 h. The gel was then washed twice in 2.5% Triton (vol/vol), rinsed 3 times quickly with distillated water, and placed 3 times for 20 min in distillated water. Each different wash was performed under gentle stirring. Gels were incubated overnight at 37° C. in 50 mM Tris buffer (containing 5 mM $CaCl_2$ and 2 µM $ZnCL_2$). Finally, gels were stained in Coomassie Blue and then destained progressively until bands of lysis (enzyme activity) in the gels showed up as regions of negative staining The areas of lysis in the gels were analyzed using a densitometric analyzer (Bioprofil, Vilbert Lournet, Marne la vallée, France), images were taken, and band densities were measured. After treatment with bleomycin, we observed an increase in the activity of Pro-MMP-9 (100 Kd), Pro-MMP2 (72 Kd) and active MMP-2 (65 Kd). Only these MMP were quantified.

Total Lung Collagen Measurements

Aliquots of lung homogenate (50 µl) were then assayed for lung collagen levels and compared with a standard curve prepared from bovine skin using the Sircol collagen dye binding assay according to the manufacturer's instructions (Biocolor Ltd, Northern Ireland).

Alpha-I Collagen mRNA Measurement

Quantification of alpha-I collagen was described previously (26). Briefly, frozen lung samples were ground to a fine powder, and homogenized in 2 ml of Trizol reagent (In vitrogen Life technology, Paisley, UK). After vigorous shaking, chloroform was added and the samples were centrifuged at 12,000 g for 20 min. Total RNA was precipitated with isopropanol and dissolved in RNAse-free water. RNAs were reverse-transcribed into cDNA using SuperScript™$^{II}$ (Invitrogen Life technologies, Paisley, UK). Real-time quantitative PCR was performed by fluorescent dye SYBR Green methodology, using SYBR Green PCR Master Mix (Applied Biosystems) and the ABI Prism 7000 apparatus (perkin-Elmer, Foster city, CA, USA). The relative quantification of the steady-state of the target mRNA levels was calculated by an active reference, GAPDH.

Histology

After BAL and lung perfusion, the large lobe was fixed in 4% buffered formaldehyde for standard microscopic analysis. 3-µm sections were stained with Hematoxylin and Eosin (H&E) or Chromotrope Aniline Blue (CAB) as described previously (3). The severity of the morphological changes (infiltration by neutrophils and mononuclear cells, destruction and thickening of the alveolar septae and fibrosis) were assessed semi-quantitatively using a numeric fibrotic scale (Ashcroft score) (27). The mean score was considered the fibrotic score (0-8) by two independent observers (IC, BR).

Statistical Analysis

Statistical evaluation of differences between the experimental groups was determined by Mann Whitney test using Prism software. P values of <0.05 were considered statistically significant.

EXAMPLE 2

Bleomycin Induced Lung Inflammation and Fibrosis Depends on IL-1β

Bleomycin administration into the airways causes acute lung injury with inflammation with to IL-1β production, followed by chronic inflammation and fibrosis (FIGS. 1A-1F). Inflammation and fibrosis are IL-1R1-dependent as they are abrogated in IL-1R1 deficient mice and importantly the IL-1 receptor antagonist (IL-Ra), Anakinra, attenuated the lung inflammation. This part of the pathophysiology is novel and has been published (3).

Therefore, our data demonstrate that bleomycin-induced lung inflammation is mediated by to IL-1β. However, no information is available, how to IL-1β is produced. Bleomycin induced IL-1β production in the lung depends on inflammasome activation Therefore, we investigated the upstream mechanisms leading to IL-1β release and in particular the role of the inflammasome, a cytosolic complex composed of NALP3 receptor, the ASC adaptor and cysteine proteases which cleave proIL-1β into IL-1β (28). Here we find that neutrophil recruitment in BAL and lung, and the production of the inflammatory mediators KC and IL-6 (FIGS. 2A-2D) and of IL-1β and the profibrotic mediator TIMP-1 (FIGS. 2E, 2F) were significantly reduced in NALP3 and ASC deficient mice. Therefore, the data indicate that the NALP3 inflammasome is activated upon bleomycin tissue injury resulting in IL-1β maturation and subsequent inflammation.

EXAMPLE 3

Uric Acid is Produced in the Lung Upon Bleomycin Administration and Inhibition of Uric Acid Prevents Lung Inflammation a) Which Mediator Causes the NALP3 Inflammasome Activation and Focused on Uric Acid The inventors have demonstrated that uric acid production was enhanced in the bronchoalveolar lavage fluid (BALF) (FIG. 3A) and in the lung (FIG. 3B) after bleomycin in comparison to saline.

b) Whether Inhibition of Uric Acid Levels Reduces Inflammation

Figure 3A:
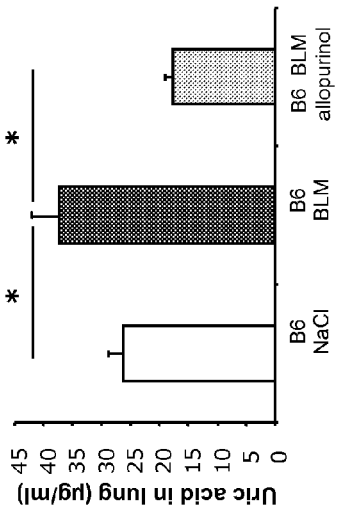
Figure 3B:
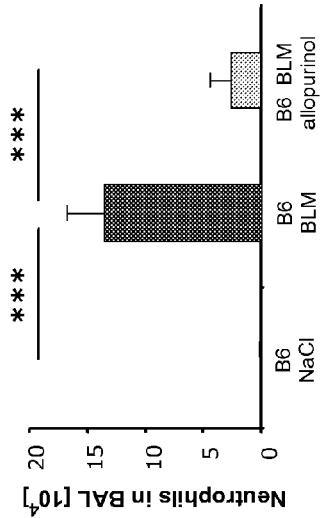
Figure 3C:
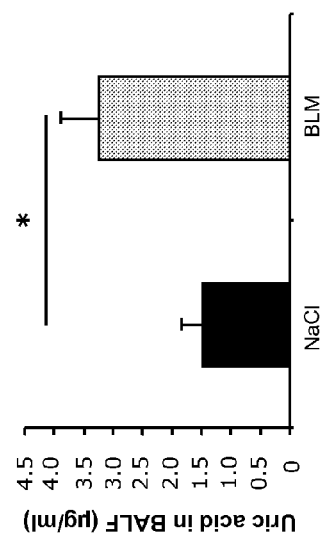
Figure 3D:
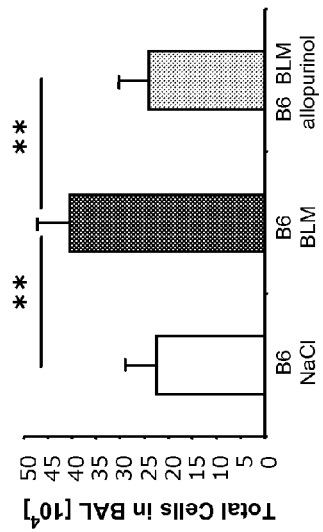
Figure 3E:
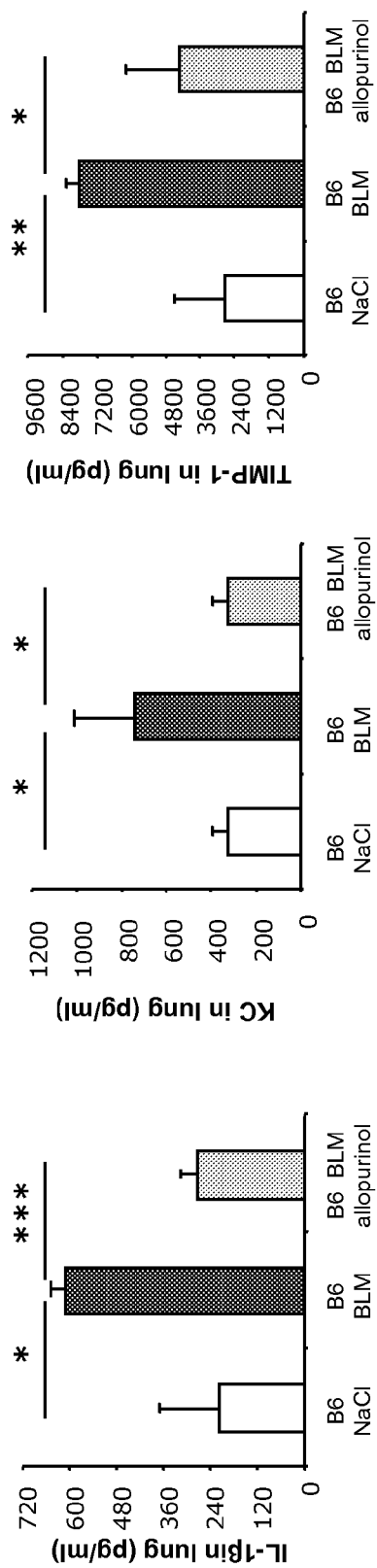
Figure 4A:
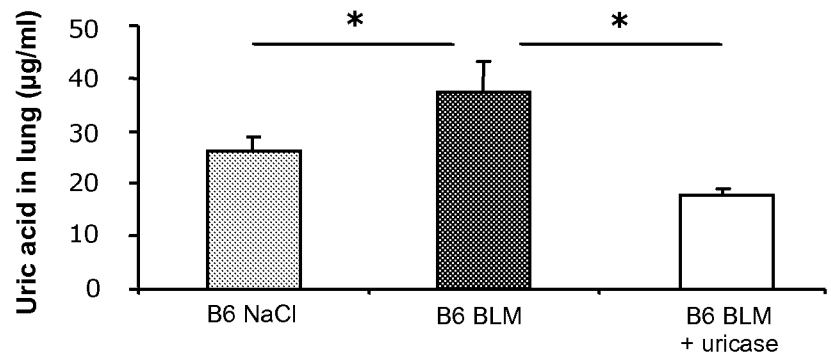

First, the inventors have shown that systemic administration of xanthine oxidase inhibitor allopurinol, which inhibits uric acid synthesis, prevented the increase of lung uric acid upon bleomycin (FIG. 3B).

Second, the inventors have shown that allopurinol greatly inhibited bleomycin-induced inflammation resulting in reduced total cell (FIG. 3C) and neutrophil recruitment (FIG. 3D) in the BALF.

Moreover the production of the proinflammatory and profibrotic cytokine IL-1β, the neutrophilic chemokine KC and the production of tissue inhibitor of metalloproteinase 1 (TIMP-1) involved in repair processes and characteristic of evolution to fibrosis were diminished in the lung upon allopurinol (FIGS. 3E-3F) and in the BALF upon allopurinol (data not shown).

Figure 4B:
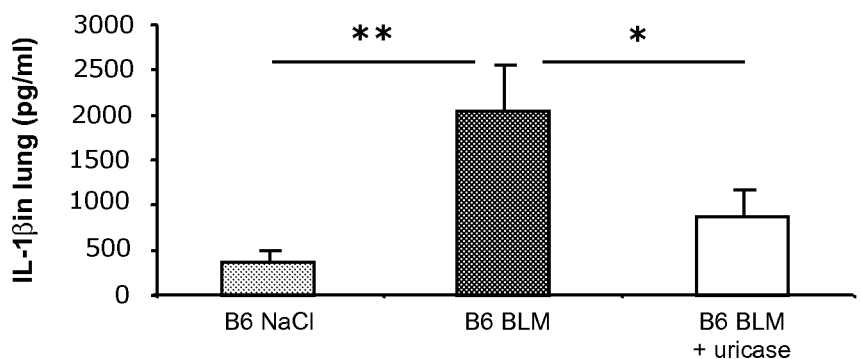
Figure 4C:
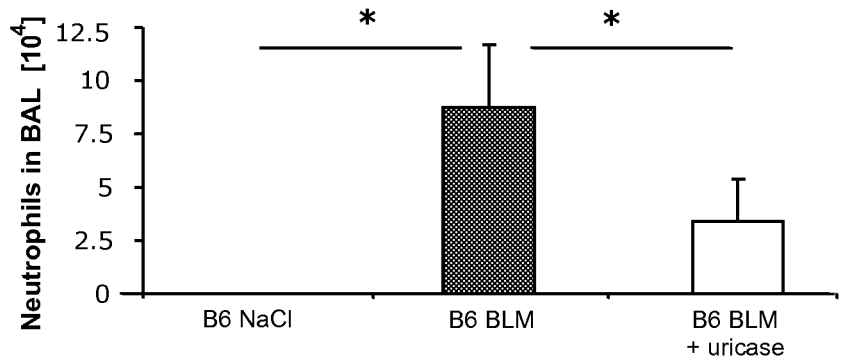

Additionally, uricase treatment, which rapidly degrades uric acid into soluble allantoin, also reduced bleomycin-induced lung uric acid increase (FIG. 4A), lung IL-1β production and neutrophil influx (FIGS. 4B, 4C).

These data demonstrate that bleomycin-induced lung inflammation and repair are mediated by uric acid. Most importantly, allopurinol or uricase administration reduces uric acid levels and inflammation. Therefore, to uric acid is a major danger signal likely released from dying pulmonary cells upon injury and that uric acid represents a new target to control inflammation upon lung injury.

EXAMPLE 4

Exogenous Uric Acid Crystals Cause Inflammation and IL-1β Production

Uric acid released from the lung upon bleomycin injury might trigger NALP3 inflammasome activation. Therefore, we asked whether exogenous uric acid given as crystals may cause lung inflammation. Upon intranasal administration uric acid crystals were found engulfed by alveolar macrophages in the airways (FIG. 5A) and induced a dose-dependent cell recruitment in the BAL (not shown), which was transient with macrophages and neutrophils reaching a maximum at 6 h, decreasing at 24 h; and the inflammation was resolved at day 14 (FIG. 5B). Allopurinol crystals which are chemically and structurally similar caused only little neutrophil recruitment into the BAL (FIG. 5C). Further, uric acid crystals induced pulmonary TIMP-1 expression, a hallmark of evolution toward fibrosis (FIG. 5D). Rapid degradation of uric acid in mice may occur due to their functional uricase, in contrast to humans (37), and repeated uric acid administration may be required to develop lung fibrosis. These data indicate for the first time that uric acid crystals induce inflammation and repair in lung similar to bleomycin.

EXAMPLE 5

Figures 6G, 6H:
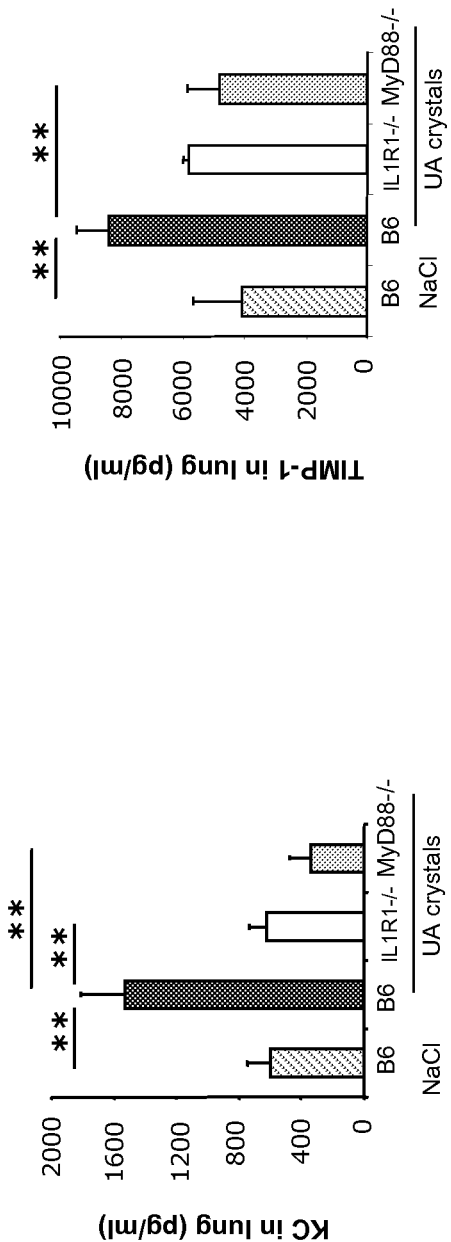

Exogenous Uric Acid Crystals Induced Inflammation Depends on The NALP3 Inflammasome a) The NALP3 Inflammasome is Involved in the Lung Inflammation Triggered by Uric Acid Crystals Exogenous uric acid crystals-induced acute lung neutrophil recruitment and IL-1β production were significantly reduced in mice deficient for the NALP3 receptor and for the ASC adaptor of the inflammasome (FIGS. 6A, 6B). Moreover, the inflammatory response to uric acid crystals was drastically reduced in MyD88 and IL-1R1 deficient mice and after IL-1Ra administration as evidenced by reduced neutrophil influx in BAL (FIGS. 6C, 6D). The inflammatory mediators, IL-1β, IL-6, KC, and TIMP-1 (FIGS. 6E-6H) were reduced in the lung of MyD88 and IL-1R1 deficient mice. IL-1β being significantly decreased in lungs from MyD88 deficient mice (FIG. 6E) suggests that other receptors using the common MyD88 adaptor such as TLR or IL-18R are involved. Previous works suggested that uric acid crystals activate TLR2 and TLR4 receptors (31) whereas other showed that these receptors are not involved in uric acid crystals-induced gout inflammation (11).
b) Role of TLR Recognition of Uric Acid Crystals The inventors have found that TLR2-4 double deficiency resulted in attenuated inflammation showing that the combined action of TLR2 and TLR4 may be required for optimal inflammation (31). Therefore uric acid crystals-induced inflammation is likely TLR2-4 dependent, but IL-18R independent, activates the NALP3 inflammasome and signals via IL-1R1/MyD88.

EXAMPLE 6

Bleomycin Activates the Inflammasome NALP3 Leading to IL-1β Production and Inflammation in Lung Intranasal administration of a single dose of bleomycin induces a rapid inflammation of the airways within 24 h, followed by tissue remodeling and lung fibrosis within 14 days. Since we showed that bleomycin-induced lung injury causes an inflammation dependent of IL-1R1 and IL-1β (3), we investigated the upstream mechanisms leading to IL-1β release and in particular the role of the inflammasome, a cytosolic multiprotein complex composed of receptors, adaptors and cysteine proteases which cleaves proIL-1β into IL-1β (28). Here we show that 24 h after bleomycin administration, neutrophil recruitment in BALF and lung (FIGS. 10A and 10B), production of the neutrophil attracting proinflammatory chemokine KC and the inflammatory mediator IL-6 (FIGS. 10C and 10D) and of the profibrotic mediators IL-1β (pro-IL-1β plus mature IL-1β) and tissue inhibitor of matrix metalloproteinase 1 (TIMP-1) (FIGS. 10E and 10F) were significantly reduced in NALP3 and ASC deficient mice. Bleomycin-induced inflammation at this time was also reduced in caspase-1 deficient mice (FIG. 11A) or in wild-type mice treated with the inhibitor of caspase-1 z-YVAD-fmk with reduced neutrophil recruitment in BALF (FIG. 11B), production of IL-1β (FIG. 11C), KC (FIG. 11D) and TIMP-1 (FIG. 11E) in the lung. The difference in IL-1β measured in lung of wild-type versus Casp-1 deficient mice or wild-type mice treated with the inhibitor of caspase-1 z-YVAD-fmk after bleomycin likely represents the maturation of IL-1β by the caspase-1 protease. Therefore, the data indicate that the NALP3 inflammasome is activated upon bleomycin lung injury resulting in enhanced production of IL-1β and subsequent inflammation.

EXAMPLE 7

Figure 12A:
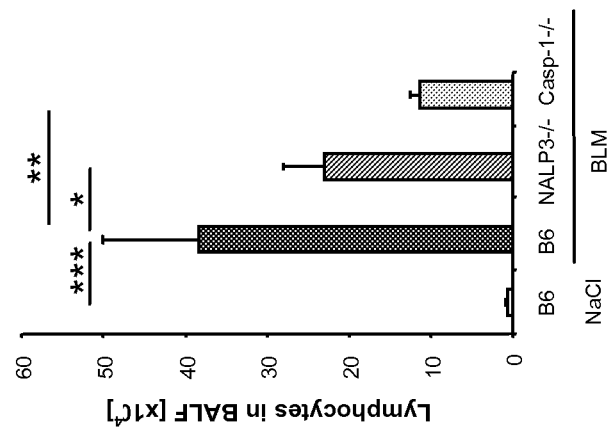
Figure 11E:
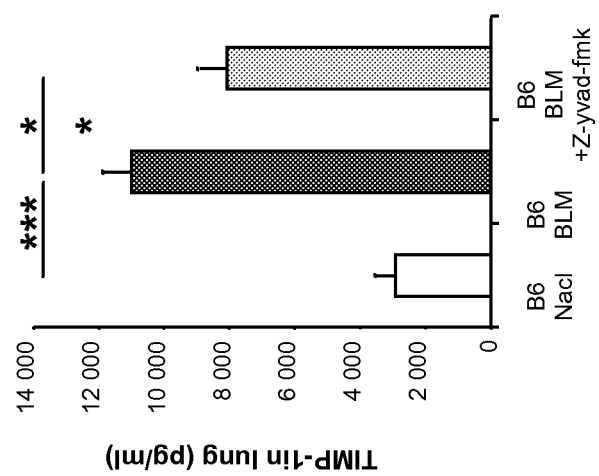
Figure 11D:
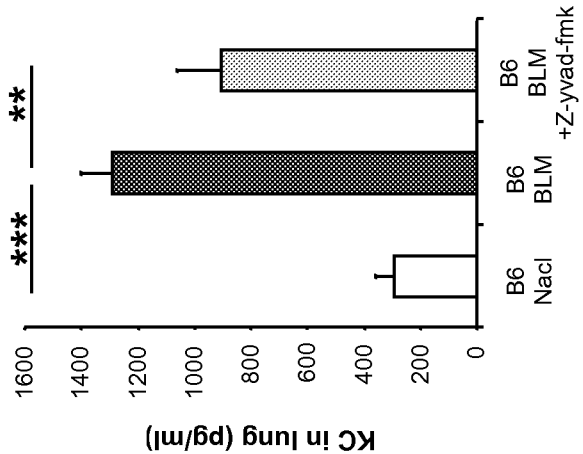
Figure 12B:
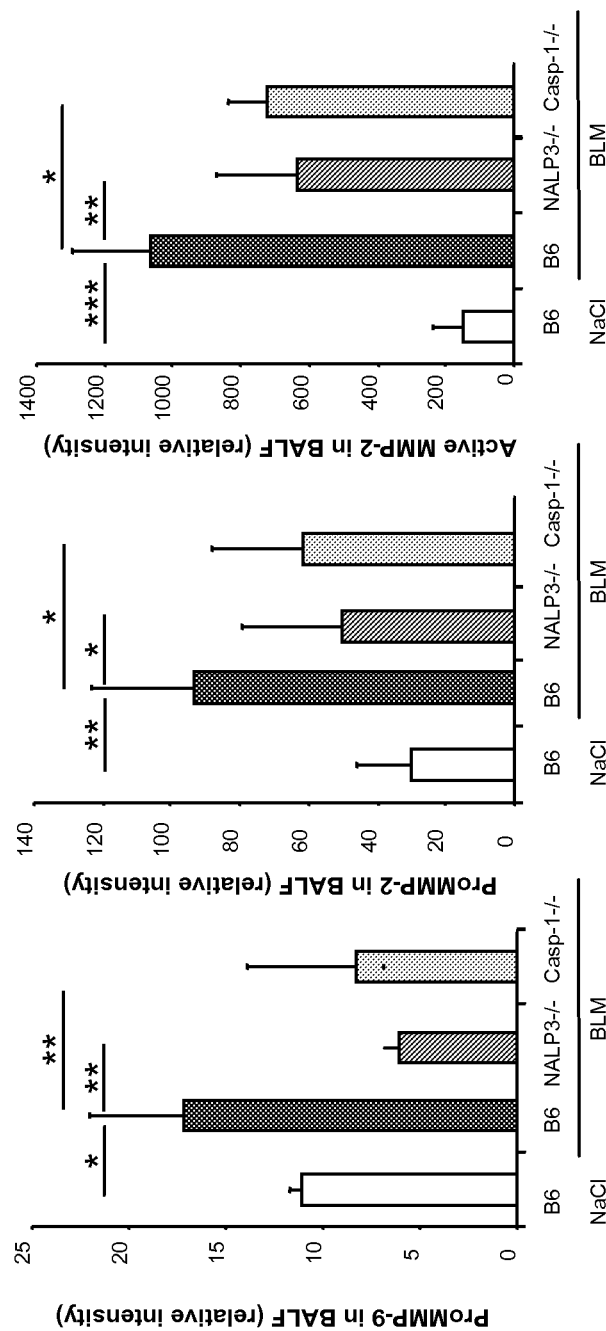
Figures 12C, 12D:
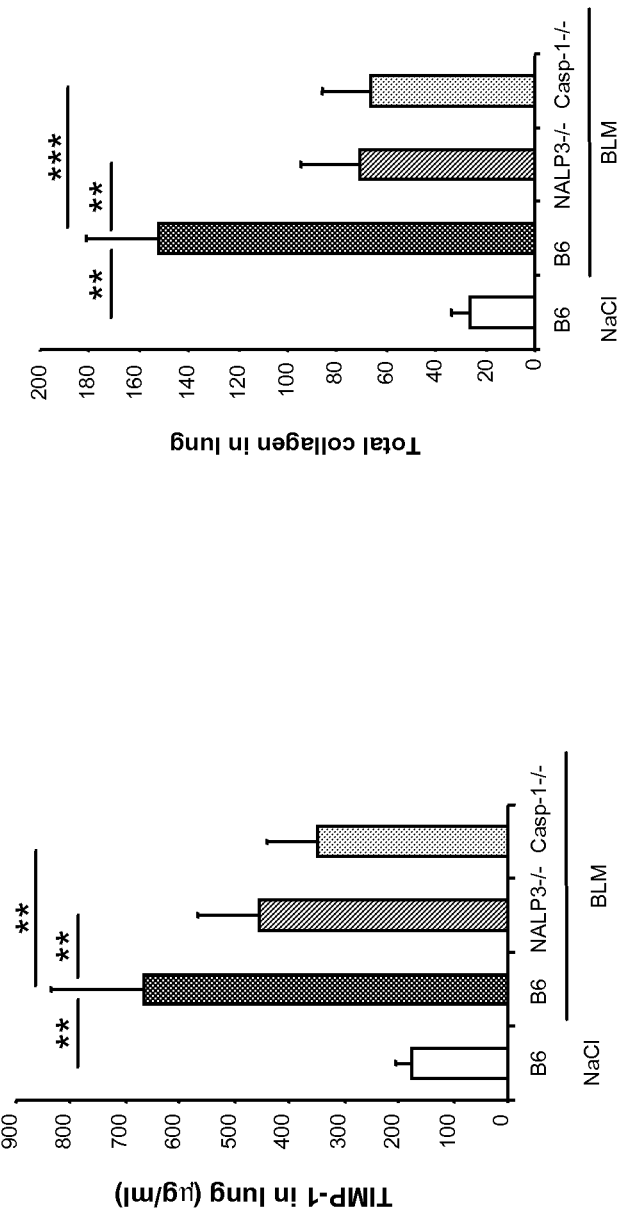

NALP3 Inflammasome is Critical for Bleomycin-Mediated Late Inflammation and Tissue Remodeling To evaluate the involvement of NALP3 inflammasome in late inflammation and tissue remodeling in lung induced by bleomycin, we analyzed cell recruitment and gelatinase activities 14 days after a single bleomycin i.n. administration by the measurement of matrix metalloproteinase 9 (MMP-9 or gelatinase A) and matrix metalloproteinase 2 (MMP-2 or gelatinase B) by zymography of the BALF. Bleomycin promoted lymphocyte recruitment into the BALF of wild-type mice which was markedly decreased in NALP3 and Casp-1 deficient mice (FIG. 12A). MMP-9 was shown to be largely produced by neutrophils and its activity was associated with neutrophil recruitment whereas MMP2 was produced by fibroblasts and associated with fibrosis (29). 14 days after bleomycin administration, Pro-MMP-9 (100 Kd) and Pro-MMP-2 (71 Kd) activities measured after activation, and active MMP-2 (65 Kd) activity were upregulated in the BALF of wild-type mice, but were significantly reduced in NALP3 and Casp-1 deficient mice (FIG. 12B). Since the balance of TIMPs and MMPs is an important factor in the fibrotic process, we analyzed the late production of TIMP-1 a hallmark for the evolution to fibrosis (26) and showed that TIMP-1 was upregulated at 14 days in lung homogenates of wild-type mice but decreased in NALP3 and Casp-1 deficient mice (FIG. 12C). Enhancement of total pulmonary collagen content upon bleomycin was attenuated in NALP3 and Casp-1 deficient mice (FIG. 12D). Therefore, late inflammation and repair processes depend on the NALP3 inflammasome.

EXAMPLE 8

Bleomycin-Induced Inflammation is Mediated by Uric Acid

Figures 13A, 13B, 13C, 13D:
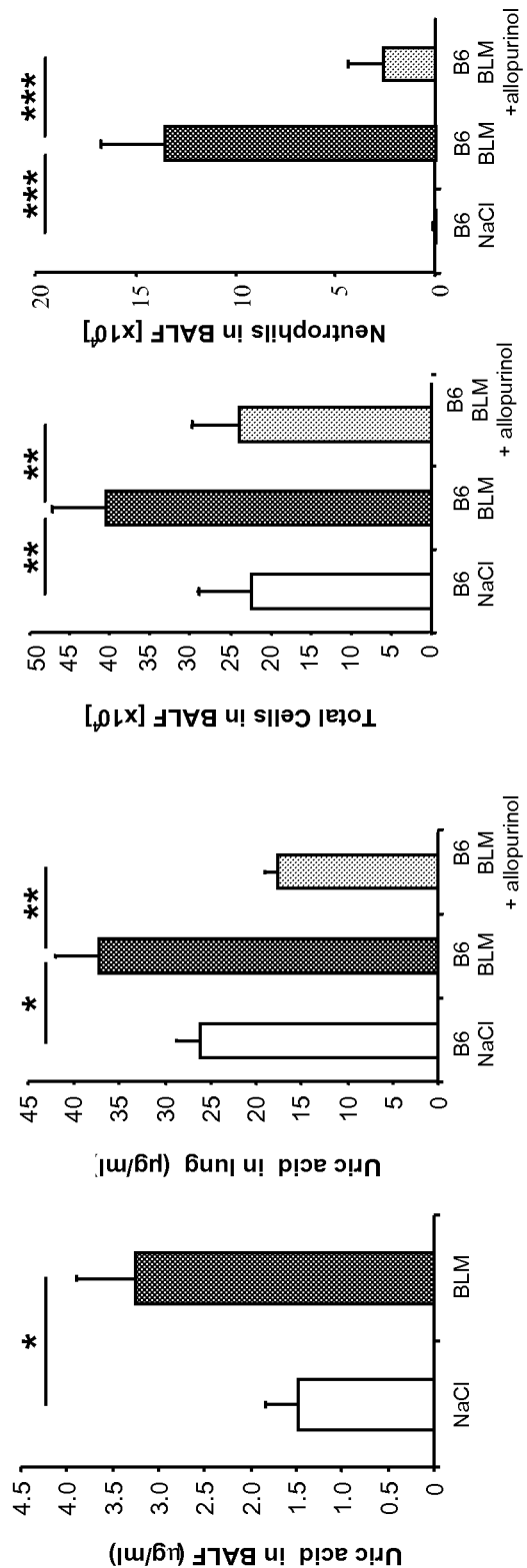
Figures 13E, 13F, 13G:
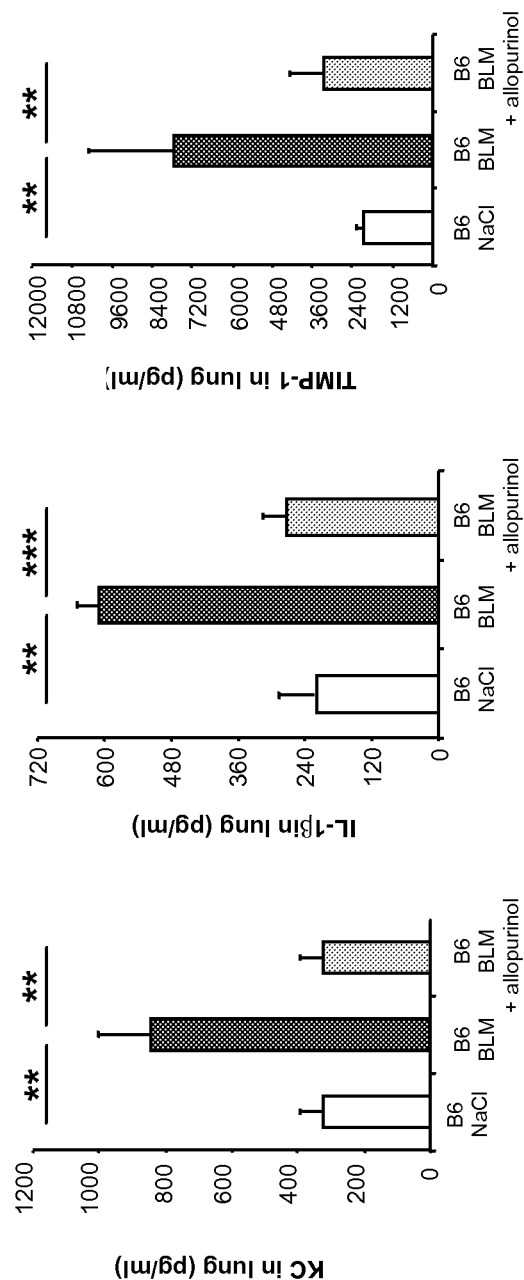

We then asked about the danger signals triggering NALP3 inflammasome activation leading to IL-1β maturation and lung inflammation upon bleomycin lung injury. In particular NALP3 is a major proinflammatory danger receptor activated by uric acid in the gout arthritis model (10). Since uric acid was identified as a principal endogenous danger signal released from injured cells, we hypothesized that uric acid can be important in induction of immunity after lung injury (16). We first assessed whether uric acid is released upon bleomycin-induced lung injury in mice. Uric acid production was enhanced in the BALF (FIG. 13A) and in the lung (FIG. 13B) 24 h after intranasal bleomycin administration (i.n.). We next assayed whether modulation of lung uric acid levels in mice airway can influence BLM-induced inflammation and remodeling. We demonstrated that s.c. administration of the xanthine oxidase inhibitor allopurinol which impairs uric acid synthesis, prevented uric acid increases in the lung upon bleomycin administration (FIG. 13B). Allopurinol greatly inhibited bleomycin-induced acute inflammation resulting in reduced total cell (FIG. 13C) and neutrophil recruitment in the BALF (FIG. 13D) and reduced production of KC in the lung (FIG. 13E). The profibrotic cytokine IL-1β (FIG. 13F) and TIMP-1 involved in repair processes and characteristic of evolution to fibrosis were diminished in the lung (FIG. 13G) and in the BALF (data not shown) upon allopurinol treatment. Further, we administered mice with uricase used to treat hyperuricemia in tumor lysis syndrome associated with cancer chemotherapy (17). Intraperitoneal or intranasal administration of uricase which rapidly degrades uric acid into soluble allantoin, also reduced bleomycin-induced lung uric acid increase (FIG. 14A), neutrophil influx (FIG. 14B) and pulmonary IL-1β production (FIG. 14C). Therefore, bleomycin-induced lung inflammation and remodeling are largely mediated by uric acid which represents a major danger signal likely released from dying pulmonary cells upon injury and a new target to control inflammation upon lung injury.

EXAMPLE 9

Bleomycin-Induced Repair and Fibrosis are Mediated by Uric Acid

Figure 15F:
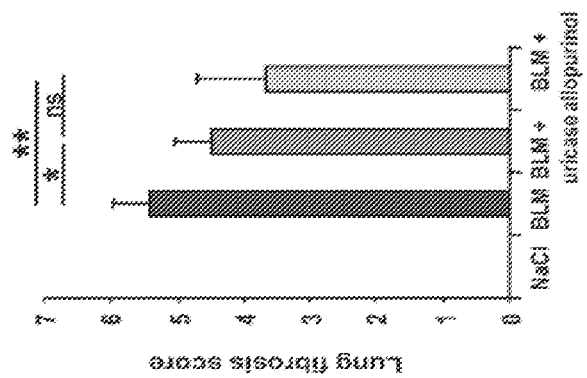
Figure 15E:
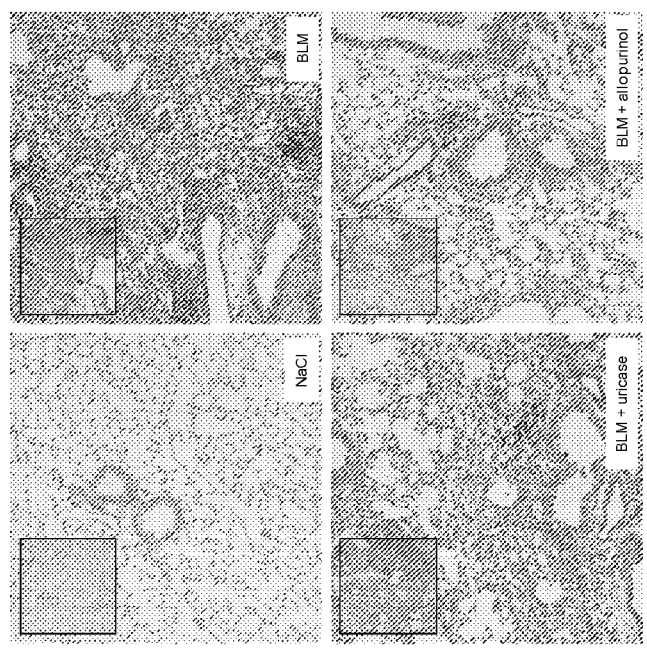
Figure 15D:
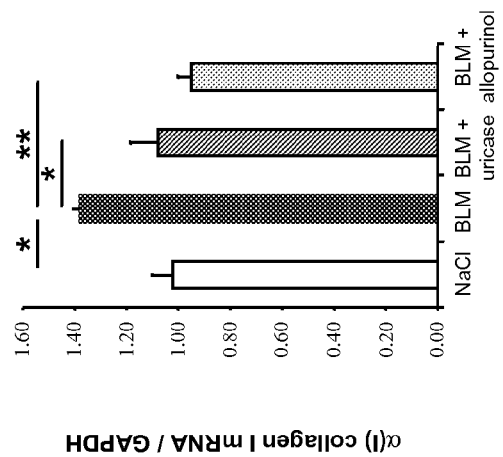

We extended our investigation to test whether the inhibition of uric acid synthesis reduces bleomycin-induced repair and fibrosis. Allopurinol (s.c.) administration reduced bleomycin-induced late lymphocyte and neutrophil recruitment in the BALF at day 8 (FIG. 15A). Gelatinase activities were assessed by the measurement of MMP-9 (gelatinase A) and MMP-2 (gelatinase B) by zymography. Pro-MMP-9 and active MMP-2 activities, which were upregulated in BALF 14 days after bleomycin administration were significantly reduced by allopurinol or uricase treatment (FIG. 15B). We then analyzed the late production of TIMP-1 and showed that TIMP-1 was upregulated at 8 days in lung homogenates (FIG. 15C) and BALF (data not shown) of bleomycin-treated mice but inhibited by allopurinol administration. Pulmonary alpha-I collagen mRNA content was increased 14 days after BLM administration, but inhibited by uricase or allopurinol treatment (FIG. 15D). Moreover, lung sections showed that BLM-induced alveolar wall destruction, collagen deposition and lung fibrosis at 14 days were significantly reduced when uric acid synthesis was inhibited or after uricase administration (FIG. 15E). The fibrosis induced by bleomycin was assessed semi-quantitatively. Fibrosis with thickening of alveolar septae and inflammation were significantly reduced in mice treated with uricase or allopurinol in comparison to B6 mice (FIG. 15F). Therefore, not only inflammation, but also repair processes and fibrosis depend on the danger signal uric acid, bridging early events to late pathology development.

EXAMPLE 10

Exogenous Uric Acid Causes Acute Lung Inflammation and Remodeling

Uric acid released from the lung upon bleomycin injury (FIG. 15A) might trigger NALP3 inflammasome activation. To validate this point, we next asked whether exogenous uric acid administration in the airways causes similar lung inflammation. Upon intranasal administration uric acid crystals were found engulfed by alveolar macrophages (FIG. 16A). They induced dose-dependent cell recruitment in the BALF with macrophages and neutrophils and few lymphocytes (FIG. 16B), whereas the chemically and structurally similar allopurinol crystals caused only little neutrophil recruitment into the BALF (FIG. 16C). The inflammation was transient, reaching a maximum at 6 h, decreasing at day 1 and being resolved at day 14 (FIG. 16D). Further, uric acid crystals dose-dependently induced pulmonary TIMP-1, a marker of incipient fibrosis (FIG. 16E), which returned to basal levels at day 14 (data not shown), as reported after exogenous IL-1β, whereas bleomycin administration induced a long lasting production of TIMP-1(3). Rapid degradation of uric acid occurs in mice due to their functional uricase, in contrast to humans (30), and repeated uric acid crystal administration may be required to develop lung fibrosis. Thus, local administration of uric acid crystals triggers inflammation and repair in the lung, similar to bleomycin.

EXAMPLE 11

Uric Acid-Induced Acute Lung Inflammation is Dependent Upon Inflammasome and MyD88/IL-1R1

Figure 18A:
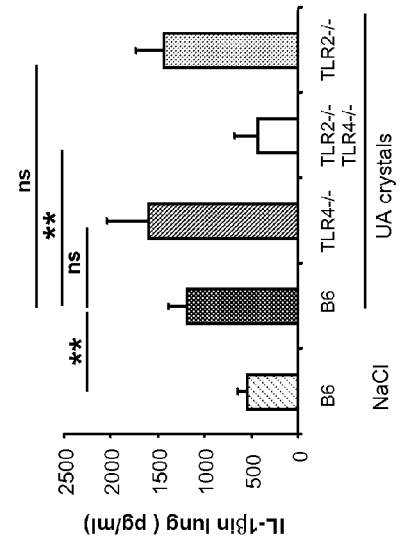
Figure 18B:
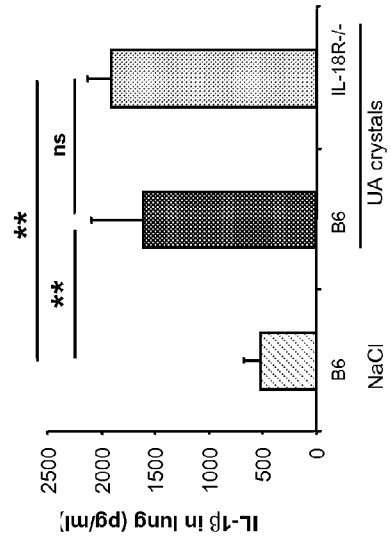
Figure 18C:
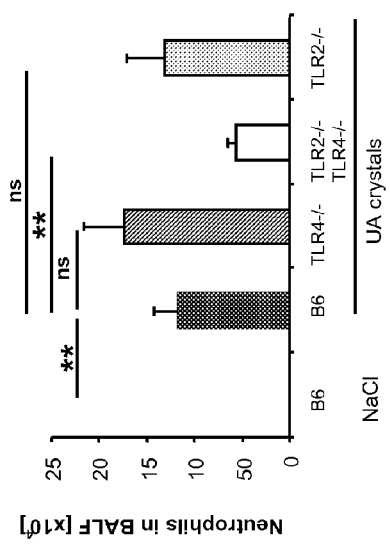
Figure 18D:
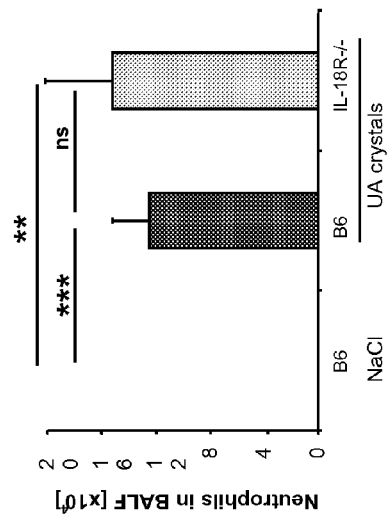

We then investigated whether the NALP3 inflammasome was involved in the lung inflammation triggered by uric acid crystals. Acute lung neutrophil recruitment (FIGS. 17A and 17C) and IL-1β production (FIGS. 17B and 17D) induced 6 h after exogenous uric acid crystals administration, were significantly reduced in mice deficient for the inflammasome NALP3 receptor or ASC adaptor in comparison to wild-type mice. Moreover, the inflammatory response to uric acid crystals was drastically reduced in MyD88 and IL-1R1 deficient mice (FIG. 17E) or after IL-1 neutralization by IL-1Ra administration (FIG. 17F) as evidenced by reduced neutrophil influx in BALF. The inflammatory mediators IL-6 (FIG. 17G) and KC (FIG. 17H) and the fibrotic mediator TIMP-1 (FIG. 17I) induced by uric acid crystals were reduced in the lung of MyD88 and IL-1R1 deficient mice. IL-1β was significantly decreased in lungs from MyD88 deficient mice but not from IL-1R1 deficient mice (FIG. 17J) suggesting that other receptors using the common MyD88 adaptor such as TLR or IL-18R may be involved. Previous works proposed that uric acid crystals activate TLR2 and TLR4 receptors (31) whereas others showed that these receptors are not involved in uric acid crystals-induced inflammation (11). We show here that mice deficient for either TLR2 or TLR4 developed inflammation in response to uric acid crystals (FIGS. 18A and 18B), as did IL-18R deficient mice (FIGS. 18C and 18D). However mice deficient for both TLR2 and TLR4 displayed an attenuated inflammatory response (FIGS. 18A and 18B) showing that the combined action of TLR2 and TLR4 may be required for optimal inflammation in response to uric acid crystals. Therefore uric acid crystals-induced inflammation is likely TLR2/TLR4 dependent, but IL-18R independent, and activates the NALP3 inflammasome and signals via IL-1R1/MyD88.

Here, using lung injury induced by bleomycin, we present evidence that uric acid is locally released and activates the NALP3 inflammasome resulting in IL-1β production. We show that bleomycin-induced lung injury resulting in IL-1β production and subsequent inflammation is dependent on the inflammasome NALP3 and ASC. The partial decrease in IL-1β measured in lung of NALP3 deficient versus wild-type mice after bleomycin may represent a direct defect in the maturation of IL-1β by the NALP3 inflammasome or some indirect effects. Indeed production of pro-IL-1β, known to be independent on NALP3 inflammasome, maturation in IL-1β which depends on inflammasome activation, and secretion of mature IL-1β, are separate processes allowing to tightly regulate the production of such a powerful inflammatory cytokine We verified the implication of caspase-1 in the bleomycin-induced inflammation and confirmed the role of the NALP3 inflammasome in this pathology. We demonstrate that lung injury results in local accumulation of uric acid which acts as an endogenous danger signal probably activating the NALP3 inflammation and leading to IL-1β dependent inflammation. Here we show that regulation of uric acid levels either by xanthine oxidase inhibition with allopurinol or degradation of uric acid by uricase abrogate inflammation and reduce remodeling and fibrosis upon bleomycin-induced lung injury. Treatment with uricase confirms that reducing local uric acid levels attenuates inflammation and remodeling. Inflammation, but also repair processes and fibrosis depend on the danger signal uric acid, bridging early events to further pathology development. Our data provide evidence that the NALP3 inflammasome is activated by uric acid. The fact that uricase and allopurinol inhibit bleomycin-induced inflammation and fibrosis represent compelling evidence that uric acid plays a critical role in bleomycin-induced lung pathology.

Exogenous uric acid crystals have been shown to activate the NALP3 inflammasome leading to IL-1β-dependent inflammation in the peritoneal cavity (10, 11). Here we demonstrate exogenous uric acid crystals given by the airways cause NALP3 inflammasome activation, the production of IL-1β, IL-1R1/MyD88 dependent lung inflammation and TIMP-1 expression, a hallmark for the evolution to fibrosis (26). IL-18R, TLR2 and TLR4 are dispensable for lung inflammation to exogenous uric acid crystals. Nevertheless, we observed that the combined action of TLR2 and TLR4 is required for optimal inflammation in response to uric acid crystals as showed in lung inflammation caused by airway administration of dying cells (34). This requirement for either TLR2 or TLR4 was also shown in response to peritoneal administration of dying cell (15) which probably release uric acid as reported by the same group (16). TLR2 and TLR4 may be involved in the generation of the pro-IL-1β upon uric acid crystals stimulation and maturated after uric acid crystal-mediated activation of the NALP3 inflammasome (10). Our data demonstrates the possibility that regulating uric acid production at the level of synthesis or metabolism might be particularly useful in limiting chronic lung inflammation, repair and fibrosis. Indeed, allopurinol is currently used to treat gout, and uricase is an alternative therapy of acute gout arthritis (35) or hyperuricemic syndromes (17). In an attempt to summarize our data, we propose the model presented in FIG. 10. Bleomycin-induced injury of lung cells, probably epithelial cells induces activation of the NALP3 inflammasome leading to lung IL-1β production, inflammation and remodeling. Bleomycin-induced cell injury results in release of uric acid which represents a major danger/stress signal likely generated from dying pulmonary cells upon injury. Local increase probably induces uric acid crystallization. Xanthine oxidase inhibitor allopurinol which impairs uric acid synthesis or uricase which rapidly degrades uric acid into soluble allantoin, prevent uric acid release in the lung upon bleomycin and decreases IL-1β production, inflammation, remodeling and fibrosis suggesting that uric acid crystals activate the NALP3 inflammasome leading to the processing and maturation of pro-IL-1β into biologically active IL-1β. Administration of exogenous uric acid crystals induce pulmonary inflammation and remodeling typical of evolution toward fibrosis with TIMP-1 accumulation. IL-1β production, inflammation and remodeling upon uric acid crystals are dependent on the NALP3 inflammasome. TLR2 and TLR4 double deficiency impairs IL-1β production and cellular influx upon uric acid crystals and may be involved in crystal-induced production of pro-IL-1β or in uric acid crystals uptake by alveolar macrophages and/or resident cells.

Therefore, our findings provide insight into the molecular mechanisms linking tissue injury, inflammation and lung fibrosis.

Our findings support a crucial role of the NALP3 inflammasome in interstitial pulmonary fibrosis from unknown origin. We propose another mechanism whereby uric acid formation may play a pivotal role in NALP3 activation upon tissue damage-associated idiopathic lung fibrosis. Therefore, local accumulation of uric acid may act as an endogenous danger signal that activates the NALP3 inflammasome with the production of IL-1β causing lung inflammation, repair and fibrosis.

These results represent unequivocal evidence that cell death via local uric acid production causes NALP3 inflammasome activation which leads to IL-1β dependent inflammation. Furthermore, regulation of uric acid levels either by xanthine oxidase inhibition with allopurinol or degradation of uric acid by uricase abrogated inflammation and remodelling upon bleomycin-induced lung injury. Therefore uric acid represents a critical link between lung injury, NALP3 activation and IL-1β dependent inflammation. Exogenous uric acid crystals are known activators of the NALP3 inflammasome leading to IL-1β-dependent inflammation (11,40). The inventors show here that exogenous uric acid crystals in the airways induce NALP3 inflammasome activation, the production of mature IL-1β and IL-1R1/MyD88 dependent lung inflammation and TIMP-1 expression, a hallmark for the evolution to fibrosis.

These data demonstrate that regulating uric acid production at the level of synthesis by allopurinol or at the level of metabolism will be particularly useful in limiting chronic lung inflammation, repair and fibrosis. Allopurinol and uricase are currently used to treat clinical gout arthritis. The mode of action of allopurinol, a xanthine oxidase inhibitor and of uricase is given schematically in FIG. 9. Therefore, therapeutic interventions reducing uric acid levels may be of benefit in chronic lung inflammation and fibrosis.

Recent investigations suggests that tissue injury may cause sterile inflammation (15,37,32) and several mediators have been identified (33,16). Here, using lung injury induced by bleomycin the inventors have demonstrated the first and compelling evidence that uric acid is locally produced and activates the NALP3 inflammasome with the maturation of IL-1β. Previous studies showed that the intratracheal (34) or intraperitoneal administration of dying cells caused inflammation, which was independent of inflammasome/caspase-1 activation (15).

In conclusion, lung injury results in local accumulation of uric acid which acts as endogenous danger signal that activates the NALP3 inflammasome with the production of mature IL-1β causing lung inflammation, repair and fibrosis. Reduction of uric acid levels by with xanthine oxidase inhibitors compound, such as allopurinol or uricase, inhibits inflammation leading to interstitial pulmonary fibrosis. This is compelling evidence of a pivotal role of to uric acid in inflammatory pathology and opens a novel therapeutic approach of interstitial lung fibrosis.

References

1. Gross, T. J., and G. W. Hunninghake. 2001. Idiopathic pulmonary fibrosis. N Engl J Med 345(7):517-25.
2. Hamilton, R. F., Jr., L. Li, T. B. Felder, and A. Holian. 1995. Bleomycin induces apoptosis in human alveolar macrophages. Am J Physiol 269(3 Pt 1):L318-25.
3. Gasse, P., C. Mary, I. Guenon, N. Noulin, S. Charron, S. Schnyder-Candrian, B. Schnyder, S. Akira, V. F. Quesniaux, V. Lagente, B. Ryffel, and I. Couillin. 2007. IL-1R1/MyD88 signaling and the inflammasome are essential in pulmonary inflammation and fibrosis in mice. J Clin Invest 117(12):3786-99.
4. Matzinger, P. 2002. The danger model: a renewed sense of self Science 296(5566):301-5.
5. Zedler, S., and E. Faist. 2006. The impact of endogenous triggers on trauma-associated inflammation. Curr Opin Crit. Care 12(6):595-601.
6. Rock, K. L., A. Hearn, C. J. Chen, and Y. Shi. 2005. Natural endogenous adjuvants. Springer Semin Immunopathol 26(3):231-46.
7. Tian, J., A. M. Avalos, S. Y. Mao, B. Chen, K. Senthil, H. Wu, P. Parroche, S. Drabic, D. Golenbock, C. Sirois, J. Hua, L. L. An, L. Audoly, G. La Rosa, A. Bierhaus, P. Naworth, A. Marshak-Rothstein, M. K. Crow, K. A. Fitzgerald, E. Latz, P. A. Kiener, and A. J. Coyle. 2007. Toll-like receptor 9-dependent activation by DNA-containing immune complexes is mediated by HMGB1 and RAGE. Nat Immunol 8(5):487-96.
8. Yu, M., H. Wang, A. Ding, D. T. Golenbock, E. Latz, C. J. Czura, M. J. Fenton, K. J. Tracey, and H. Yang. 2006. HMGB1 signals through toll-like receptor (TLR) 4 and TLR2. Shock 26(2):174-9.
9. Scaffidi, P., T. Misteli, and M. E. Bianchi. 2002. Release of chromatin protein HMGB1 by necrotic cells triggers inflammation. Nature 418(6894):191-5.
10. Maranon, F., V. Petrilli, A. Mayor, A. Tardivel, and J. Tschopp. 2006. Gout-associated uric acid crystals activate the NALP3 inflammasome. Nature 440(7081):237-41.
11. Chen, C. J., Y. Shi, A. Hearn, K. Fitzgerald, D. Golenbock, G. Reed, S Akira, and K. L. Rock. 2006. MyD88-dependent IL-1 receptor signaling is essential for gouty inflammation stimulated by monosodium urate crystals. J Clin Invest 116(8):2262-71.
12. Mariathasan, S., D. S. Weiss, K. Newton, J. McBride, K. O'Rourke, M. Roose-Girma, W. P. Lee, Y. Weinrauch, D. M. Monack, and V. M. Dixit. 2006. Cryopyrin activates the inflammasome in response to toxins and ATP. Nature 440 (7081):228-32.
13. Sutterwala, F. S., Y. Ogura, M. Szczepanik, M. Lara-Tejero, G. S. Lichtenberger, E. P. Grant, J. Bertin, A. J. Coyle, J. E. Galan, P. W. Askenase, and R. A. Flavell. 2006. Critical role for NALP3/CIAS1/Cryopyrin in innate and adaptive immunity through its regulation of caspase-1. Immunity 24(3):317-27.
14. Watanabe, H., O. Gaide, V. Petrilli, F. Maranon, E. Contassot, S. Rogues, J. A. Kummer, J. Tschopp, and L. E. French. 2007. Activation of the IL-1beta-processing inflammasome is involved in contact hypersensitivity. J Invest Dermatol 127(8):1956-63.
15. Chen, C. J., H. Kono, D. Golenbock, G. Reed, S. Akira, and K. L. Rock. 2007. Identification of a key pathway required for the sterile inflammatory response triggered by dying cells. Nat Med 13(7):851-6.
16. Shi, Y., J. E. Evans, and K. L. Rock. 2003. Molecular identification of a danger signal that alerts the immune system to dying cells. Nature 425(6957):516-21.
17. Cammalleri, L., and M. Malaguarnera. 2007. Rasburicase represents a new tool for hyperuricemia in tumor lysis syndrome and in gout. Int J Med Sci 4(2):83-93.
18. Gasse, P., N. Riteau, V. Petrilli, J. Tschopp, V. Lagente, V. F. Quesniaux, B. Ryffel, and I. Couillin. 2008. Uric acid is a danger signal activating NALP3 inflammasome in lung injury inflammation and fibrosis. Rev Mal Respir 25(9): 1191.
19. Kawai, T., O. Adachi, T. Ogawa, K. Takeda, and S. Akira 1999. Unresponsiveness of MyD88-deficient mice to endotoxin. Immunity 11(1):115-22.
20. Labow, M., D. Shuster, M. Zetterstrom, P. Nunes, R. Terry, E. B. Cullinan, T. Bartfai, C. Solorzano, L. L. Moldawer, R. Chizzonite, and K. W. McIntyre. 1997. Absence of IL-1 signaling and reduced inflammatory response in IL-1 type I receptor-deficient mice. J Immunol 159(5):2452-61.
21. Hoshino, K., H. Tsutsui, T. Kawai, K. Takeda, K. Nakanishi, Y. Takeda, and S. Akira. 1999. Cutting edge: generation of IL-18 receptor-deficient mice: evidence for IL-1 receptor-related protein as an essential IL-18 binding receptor. J Immunol 162(9):5041-4.
22. Kuida, K., J. A. Lippke, G. Ku, M. W. Harding, D. J. Livingston, M. S. Su, and R. A. Flavell. 1995. Altered cytokine export and apoptosis in mice deficient in interleukin-1 beta converting enzyme. Science 267(5206):2000-3.
23. Hoshino, K., O. Takeuchi, T. Kawai, H. Sanjo, T. Ogawa, Y. Takeda, K. Takeda, and S. Akira 1999. Cutting edge: Toll-like receptor 4 (TLR4)-deficient mice are hyporesponsive to lipopolysaccharide: evidence for TLR4 as the Lps gene product. J Immunol 162(7):3749-52.
24. Takeuchi, O., K. Hoshino, T. Kawai, H. Sanjo, H. Takada, T. Ogawa, K. Takeda, and S. Akira 1999. Differential roles of TLR2 and TLR4 in recognition of gram-negative and gram-positive bacterial cell wall components. Immunity 11(4):443-51.
25. Mariathasan, S., K. Newton, D. M. Monack, D. Vucic, D. M. French, W. P. Lee, M. Roose-Girma, S. Erickson, and V. M. Dixit. 2004. Differential activation of the inflammasome by caspase-1 adaptors ASC and Ipaf. Nature 430 (6996):213-8.
26. Manoury, B., S. Caulet-Maugendre, I. Guenon, V. Lagente, and E. Boichot. 2006. TIMP-1 is a key factor of fibrogenic response to bleomycin in mouse lung. Int J Immunopathol Pharmacol 19(3):471-87.
27. Ashcroft, T., J. M. Simpson, and V. Timbrell. 1988. Simple method of estimating severity of pulmonary fibrosis on a numerical scale. J Clin Pathol 41(4):467-70.
28. Mariathasan, S., and D. M. Monack. 2007. Inflammasome adaptors and sensors: intracellular regulators of infection and inflammation. Nat Rev Immunol 7(1):31-40.
29. Corbel, M., C. Belleguic, E. Boichot, and V. Lagente. 2002. Involvement of gelatinases (MMP-2 and MMP-9) in the development of airway inflammation and pulmonary fibrosis. Cell Biol Toxicol 18(1):51-61.
30. Wu, X., M. Wakamiya, S. Vaishnav, R. Geske, C. Montgomery, Jr., P. Jones, A. Bradley, and C. T. Caskey. 1994. Hyperuricemia and urate nephropathy in urate oxidase-deficient mice. Proc Natl Acad Sci USA 91(2):742-6.
31. Liu-Bryan, R., P. Scott, A. Sydlaske, D. M. Rose, and R. Terkeltaub. 2005. Innate immunity conferred by Toll-like receptors 2 and 4 and myeloid differentiation factor 88 expression is pivotal to monosodium urate monohydrate crystal-induced inflammation. Arthritis Rheum 52(9):2936-46.
32. Sauter, B., M. L. Albert, L. Francisco, M. Larsson, S. Somersan, and N. Bhardwaj. 2000. Consequences of cell death: exposure to necrotic tumor cells, but not primary tissue cells or apoptotic cells, induces the maturation of immunostimulatory dendritic cells. J Exp Med 191(3):423-34.
33. Bianchi, M. E. 2007. DAMPs, PAMPs and alarmins: all we need to know about danger. J Leukoc Biol 81(1):1-5.
34. Wang, L., J. F. Scabilloni, J. M. Antonini, Y. Rojanasakul, V. Castranova, and R. R. Mercer. 2006. Induction of secondary apoptosis, inflammation, and lung fibrosis after intratracheal instillation of apoptotic cells in rats. Am J Physiol Lung Cell Mol Physiol 290(4):L695-L702.
35. Moolenburgh, J. D., M. K. Reinders, and T. L. Jansen. 2006. Rasburicase treatment in severe tophaceous gout: a novel therapeutic option. Clin Rheumatol 25(5):749-52.
36. Feldmeyer, L., Keller, M., Niklaus, G., Hohl, D., Werner, S., and Beer, H. D. (2007). The inflammasome mediates UVB-induced activation and secretion of interleukin-1beta by keratinocytes. Curr Biol 17, 1140-1145.
37. Gallucci, S., Lolkema, M., and Matzinger, P. (1999). Natural adjuvants: endogenous activators of dendritic cells. Nat Med 5, 1249-1255.
38. Wang, R., Ibarra-Sunga, O., Verlinski, L., Pick, R., and Uhal, B. D. (2000). Abrogation of bleomycin-induced epithelial apoptosis and lung fibrosis by captopril or by a caspase inhibitor. Am. J. Physiol. Lung Cell. Mol. Physiol. 279, L143-151.
39. Vogl, T., Tenbrock, K., Ludwig, S., Leukert, N., Ehrhardt, C., van Zoelen, M. A., Nacken, W., Foell, D., van der Poll, T., Sorg, C., and Roth, J. (2007). Mrp8 and Mrp14 are endogenous activators of Toll-like receptor 4, promoting lethal, endotoxin-induced shock. Nat. Med. 13, 1042-1049.
40. Maranon, F., Petrilli, V., Mayor, A., Tardivel, A., and Tschopp, J. (2006). Gout-associated uric acid crystals activate the NALP3 inflammasome. Nature 440, 237-241. Matzinger, P. (2002). The danger model: a renewed sense of self. Science 296, 301-305.

The invention claimed is:

1. A method for the prevention and/or the treatment of IL-1β driven lung pathology in a mammal in need thereof, comprising the step of administering an effective amount of a compound capable of reducing the uric acid level in said mammal, wherein said compound is selected from the group consisting of:
   an uricase, a recombinant uricase, and a functional fragment thereof, and
   an uricosuric compound, an inhibitor of the tubular organic anion transporter resulting in the augmentation of renal elimination of uric acid, and a pharmaceutically acceptable salt thereof.

2. A method according to claim 1, wherein said IL-1β driven lung pathology is selected from the group consisting of lung inflammation, lung fibrosis and lung pathologies from autoimmune origin.

3. A method according to claim 1, wherein said IL-1β driven lung pathology is a lung inflammation leading to fibrosis and respiratory failure.

4. A method according to claim 1, wherein said recombinant uricase is rasburicase.

5. A method according to claim 4, wherein said uricase is pegylated.

6. A method according to claim 1, wherein said uricosuric compound or inhibitor of the tubular organic anion transporter resulting in the augmentation of renal elimination of uric acid is selected from the group consisting of probenecid, benzbromarone, sulfinpyrazone, thromboxane synthetase inhibitors and thromboxane receptor antagonists.

7. A method according to claim 1, wherein said composition is administered by intravenous injection, by intramuscular injection or orally.

8. A method according to claim 2, wherein lung fibrosis is selected from the group consisting of chronic fibrosis, chronic obstructive pulmonary disease (COPD) and interstitial fibrosis.

* * * * *